(12) United States Patent
Shamblott et al.

(10) Patent No.: US 7,795,026 B2
(45) Date of Patent: Sep. 14, 2010

(54) METHODS FOR OBTAINING HUMAN EMBRYOID BODY-DERIVED CELLS

(75) Inventors: Michael J. Shamblott, Baltimore, MD (US); John D. Gearhart, Baltimore, MD (US)

(73) Assignee: The Johns Hopkins University School of Medicine, Baltimore, MD (US)

( * ) Notice: Subject to any disclaimer, the term of this patent is extended or adjusted under 35 U.S.C. 154(b) by 579 days.

(21) Appl. No.: 09/767,421

(22) Filed: Jan. 22, 2001

(65) Prior Publication Data

US 2003/0175954 A1  Sep. 18, 2003

Related U.S. Application Data

(60) Provisional application No. 60/177,287, filed on Jan. 21, 2000.

(51) Int. Cl.
*C12N 5/02* (2006.01)
(52) U.S. Cl. ................ 435/384; 435/377; 435/379; 435/381
(58) Field of Classification Search ........... 435/366, 435/375, 377, 333, 325, 373, 383
See application file for complete search history.

(56) References Cited

U.S. PATENT DOCUMENTS 5,453,357 A * 9/1995 Hogan .................. 435/7.21
6,090,622 A    7/2000 Gearhart et al.

OTHER PUBLICATIONS

Allsopp et al. Evidence for a Critical Telomere Length in Senescent Human Fibroblasts. Exper. Cell Res. 1995, vol. 219, pp. 130-136.*
Lefebvre et al. Culture of Adult Human Islet Preparations with Hepatocyte Growth Factor and 804G Matrix is Mitogenic for Duct Cells but Not for Beta-Cells. Diabetes. 1998, vol. 47, pp. 134-137.*
Jin et al. Proliferation and Differentiation of Human Fetal Myoblasts is Regulated by PSGF-BB. Differentiation. 1993, vol. 54, pp. 47-54.*
Suzuki et al. The Human GATA-6 Gene: Structure, Chromosomal Location, and Regulation of Expression by Tissue-Specific and Mitogen-Responsive Signals. Genomics. 1996, vol. 38, pp. 283-290.*
Damjanov et al. Retinoic Acid-Induced Differentiation of the Developmentally Pluripotent Human Germ Cell Tumor-Derived Cell Line, NCCIT. Laboratory Invest. 1993, vol. 68, pp. 220-232.*
Li et al. Human Pediatric and Adult Ventricular Cardiomyocytes in Culture: Assessment of Phenotypic Changes with Passaging. Cardiovascular Res. 1996, vol. 32, pp. 362-373.*
Koshimizu, Uichi et al., "Functional Requirement of gp130-Mediated Signaling for Growth and Survival of Mouse Primordial Germ Cells in vitro and Derivation of Embryonic Germ (EG) Cells," *Development*, vol. 122, pp. 1235-1242, 1996.
Olie, Ra et al., "Heterogeneity in the in vitro Survival and Proliferation of Human Seminoma Cells," *British Journal of Cancer*, vol. 71, pp. 13-17, 1995.

Shamblott, Michael J. et al., "Properties of Cell LinesDerived from Human Primordial Germ Cells," *Molecular Biology of the Cell*, vol. 8, p. 223A, Nov. 1997.
Wang, S. et al., "Neural Cells Derived in Culture from Human Embryonic Germ (EG) Cells," *Molecular Biology of the Cell*, vol. 9, p. 437A, Nov. 1998.
Braun, T., et al., "*Myf-6*, A New Member of the Human Gene Family of Myogenic Determination Factors: Evidence for a Gene Cluster on Chromosome 12," The EMBO Journal, 9:(22) pp. 821-831, 1990.
Rohwedel, Jurgen, et al., "Primordial Germ Cell-Derived Mouse Embryonic Germ (EG) Cells In Vitro Resemble Undifferentiated Stem Cells with Respect To Differentiation Capacity and Cell Cycle Distribution," Cell Biology International 20:(8)579-587, 1996.
Schuldiner, Maya, et al., "Effects of Eight Growth Factors on the Differentiation of Cells Derived from Human Embryonic Stem Cells," PNAS, 97:(21)11307-11312, 2000.
Shamblott, Michael J., et al., "Derivation of Pluripotent Stem Cells from Cultured Human Primordial Germ Cells," Proc. Natl. Acad. Sci. USA vol. 95, 13726-13731, 1998.
Shamblott, Michael J., et al., "Human Embryonic Germ Cell Derivatives Express a Broad Range of Developmentally Distinct Markers and Proliferate EXtensively in vitro," PNAS, 98:(1)113-118, 2001.
Shamblott, Michael J., et al., "Pluripotent Stem Cells," Prin. Of Tissue Engineering, $2^{nd}$ Ed., Academic Press, Chap. 29, pp. 369-381, 2000.
Shim, Hosup, et al., "Isolation of Pluripotent Stem Cells from Cultured Porcine Primordial Germ Cells," Biology of Reproduction 57, pp. 1089-1095, 1997.
Tohyama, Takashi, et al., Nestin Expression in Embryonic Human Neuroepithelium and in Human Neuroepithelial Tumor Cells, Laboratory Investigation, 66:(3)303-313, 1992.
Topp, W., et al., "In Vitro Differentiation of Teratomas and the Distribution of Creatine Phosphokinase and Plasminogen Activator in Teratocarcinoma-Derived Cells," Cancer Res. vol. 36, pp. 4217-4223, 1976.
Yuen, David, et al. "Generation of a Primitive Erythroid Cell Line and Promotion of Its Growth by Basic Fibroblast Growth Factor," Blood, 91:(9)3202-3209, 1998.

(Continued)

*Primary Examiner*—Deborah Crouch
(74) *Attorney, Agent, or Firm*—DLA Piper LLP (US)

(57) ABSTRACT

The invention is directed to novel cells that are derived from human embryoid bodies. Such embryoid body-derived (EBD) cells are relatively uncommitted or progenitor (e.g., pluripotent) cells. EBD cells, while not immortal, display long-term proliferation in culture with a normal karyotype and can be cryopreserved and cloned. They can be efficiently transfected with retroviruses and lentivirus and genetically manipulated. Although they have a developmentally broad multilineage expression profile, they do not form tumors when injected into severe combined immunodeficiency (SCID) mice. As a result, EBD cells have a variety of uses, for example, in transplantation therapies.

11 Claims, 2 Drawing Sheets

OTHER PUBLICATIONS

Itskovitz-Eldor, J. et al., "Differentiation of Human Embryonic Stem Cells into Embryoid Bodies Comprising the Three Embryonic Germ Layers", *Molecular Medicine*, vol. 6, No. 2, pp. 88-95, 2000.

Rathjen, P.D. et al., "Properties and uses of embryonic stem cells: prospects for application to human biology and gene therapy", *Reproduction, Fertility and Development*, vol. 10, No. 1, pp. 31-47, 1998.

Reubinoff, Benjamin E. et al, "Embryonic stem cell lines from human blastocysts: somatic differentiation in vitro", *Nature Biotechnology*, vol. 18, No. 4, pp. 399-404, 2000.

Wang, S. et al., "Neural Cells Derived in Culture from Human Embryonic Germ (EG) Cells", *Molecular Biology of the Cell*, vol. 9, No. Suppl., pp. 437A, 1998.

* cited by examiner

METHODS FOR OBTAINING HUMAN EMBRYOID BODY-DERIVED CELLS

CROSS-REFERENCE TO RELATED APPLICATIONS

This application incorporates by reference and claims the benefit of priority under 35 U.S.C. §119(e) of U.S. Provisional Application No. 60/177,287, filed Jan. 21, 2000. The aforementioned application is explicitly incorporated herein by reference in its entirety and for all purposes.

TECHNICAL FIELD OF THE INVENTION

The invention relates generally to the fields of cell biology and tissue regeneration. More specifically, the invention is derived to novel human embryoid bodies (EBs), novel undifferentiated human cells derived therefrom, called embryoid body-derived (EBD) cells, and related in vitro methods for producing EBs and EBD cells and using such cells. The invention has applications in the areas of cell culture, tissue transplantation, tissue engineering, drug discovery and gene therapy.

BACKGROUND

There is an increasing need to find sources of human stem cells, other than fetal tissue, that can be used to regenerate tissues and organs. A source of cell lines that are relatively uncommitted or progenitors (e.g., pluropotent) could provide an enlarged supply of stem cells for use in somatic transplantation or organ regeneration therapies, for examples.

Mouse pluropotent stem cells (mPSC) have been derived from the inner cell mass cells of blastocysts and from primordial germ cells colonizing the developing gonadal ridge and are referred to as embryonic stem (ES) cells and embryonic germ (EG) cells. When mPSCs differentiate in vitro, they form complex three-dimensional cell aggregates termed embryoid bodies (EBs). Some early developmental processes are recapitulated within the environment of an EB, resulting in a haphazard collection of precursor and more fully differentiated cells from a wide variety of lineages. Through this intermediate step, mPSCs can generate cells of the hematopoietic lineage (Wiles and Keller, *Development* [Cambridge, U.K.], 111:259-267, 1991 Keller et al., *Mol. Cell. Biol.* 13:473-486, 1993), cardiomyocytes (Klub et al., *Am. J. Physiol.* 269:H1913-H1921, 1995 Rohwedel et al., *Cell. Biol. Int.* 20:579-587, 1996), neurons (Bain et al., *Dev. Biol.* 168: 342-357, 1995) and glial precursors (Brustle et al., *Science* 285:754-756, 1999), skeletal muscle (Rohwedel et al., *Dev. Biol.* 164:87-101, 1994), vascular endothelial cells (Wang et al., *Development* [Cambridge, U.K.] 114:303-316, 1992), visceral endoderm (Abe et al., *Exp. Cell Res.* 229:27-34, 1996; Doetschman et al., *J. Embryol. Exp. Morphol.* 87:27-45, 1996) and glucose-responsive insulin producing cells (Soria et al., *Diabetes* 49:157-162, 2000). ES cells and EG cells differ phenotypically with respect to their culture requirements and cell surface markers, probably the result of their derivation and tissue source. ES and EG cells propagated in vitro can contribute efficiently to the formation of chimeras, including germlike chimeras.

When human EG cells differentiate, they also form EBs comprised of endodermal, ectodermal, and mesodermal derivatives (Shamblott et al., *Proc. Natl. Acad. Sci. USA* 95:13726-13732, 1998).

For a review of pluripotent stem cells, including discussions of assay methods, differentiation in vitro, and in vivo applications, see, e.g., Shamblott et al., "Pluripotent Stem Cells," in Principles of Tissue Engineering (2nd ed.), Academic Press, 2000, pp. 369-381.

SUMMARY OF THE INVENTION

The invention is directed to novel cells that are derived from human embryoid bodies (EBs), which are in turn produced by culturing EG cells. Such embryoid body derived (EBD) cells and cell lines are relatively uncommitted or progenitor cells. EBD cells, while not immortal, display robust and long-term proliferation in culture with a normal karyotype and can be cryopreserved and cloned. They can be efficiently transfected with retroviruses and lentivirus, for example, and can be genetically manipulated. Although EBD cells have a developmentally broad multilineage expression profile and do not form tumors (e.g., differentiated embryonic tumors or teratomas) when injected in vivo, such as into severe combined immunodeficiency (SCID) mice. As a result, EBD cells have a variety of uses, for example, in transplantation therapies for the treatment of such diseases as Parkinson's disease, amyotrophic lateral sclerosis (ALS), stroke, injury to motor neurons, including spinal cord injury, and diabetes.

According to one aspect of the invention, a human embryoid body-derived (EBD) cell culture is provided that comprises cells at least some of which simultaneously express polypeptide or mRNA markers that are characteristic of at least two, and in another embodiment, all three of the following cell types: ectodermal, mesodermal and endodermal cells. For example, useful ectodermal cell markers including but are not limited to nestin, vimentin, neurofilament light isoform, microtubule-associated protein 2c, tau, nonphosphorylated neurofilament heavy isoform, neuron-specific enolase, tyrosine hydroxylase, glial fibrillary acidic protein, CNPase, and galactocerebroside. Most commonly expressed are the neural markers nestin, vimentin, and glial fibrillary acidic protein, particularly nestin and vimentin, which are expressed in all EBD cell lines that we have tested. Useful mesodermal cell markers include but are not limited myf6, myosin light-chain 2 ventricular isoform, and flk1. Useful endodermal cell markers include but are not limited to α-1-fetoprotein and GATA-4. According to another aspect of the invention, at least some cells of the culture simultaneously nestin or vimentin or both, and in addition a non-ectodermal marker such as myf6, myosin light-chain 2 ventricular isoform, flk1, α-1-fetoprotein and GATA-4.

According to another aspect of the invention, EBD cultures are provided that are not immortal but that proliferate for at least thirty population doublings (PD) under suitable cell culture conditions. According to another aspect of the invention, EBD cultures proliferate under cell culture conditions that are non-permissive for proliferation of human EG cells, such as in media that lacks leukemia inhibitory factor, a fibroblast feeder layer, or both.

According to another aspect of the invention, EBD cultures are provided that comprise cells at least some of which are transfectable with a retrovirus or a lentivirus and/or do not cause formation of a teratoma when injected into a SCID mouse.

The EBD cultures of the invention may be mixed cell populations or clonal, including cultures that are clonally derived from a single EBD cell.

According to another aspect of the invention, methods of making a human EBD cell culture are provided that comprise: (a) culturing human embryonic germ (EG) cells under conditions that are suitable for formation of cystic embryoid bodies, (b) dissociating the cystic embryoid bodies to provide a constituent cell or cells, and (c) culturing the constituent cell(s) under conditions suitable to produce a human EBD cell culture as described above, such as, for example, the use of a media that includes human basic fibroblast growth factor (e.g., RPMI 1640 media supplemented with 15% fetal calf serum or EGM2MV media) and the use of a matrix, such as, for example, collagen I, human extracellular matrix, and tissue culture-treated plastic. Significantly, EBD cells proliferate on media that are not permissive for proliferation of EG cells, including for example media that lack leukemia inhibitory factor or a fibroblast feeder layer or both. Such methods optionally comprise selecting a single EBD cell from the EBD cell culture and culturing the single EBD cell to produce a clonal EBD cell culture. The EBD cell culture, whether a mixed or clonal culture, can be cultured for 30 PD or more.

According to another aspect of the invention, methods of treating a human disease or injury are provided that comprise introducing a composition comprising an EBD cell or EBD cell culture into the body of a patient having the disease or injury.

A number of embodiments of the present invention have been described. Nevertheless, it will be understood that various modifications may be made without departing from the spirit and scope of the invention. Accordingly, other embodiments are within the scope of the following claims.

All publications, patents and patent applications cited herein are hereby expressly incorporated by reference for all purposes.

The details of one or more embodiments of the invention are set forth in the accompanying drawings and the description below. Other features, objects, and advantages of the invention will be apparent from the description and drawings, and from the claims.

DESCRIPTION OF DRAWINGS

FIG. 2 shows the mRNA expression profiles of thirteen LVEC clonal cell lines and two LVEC cultures. Cells were grown in EGM2MV media on collagen I. Markers and lineages are listed above and are grouped by lineage affiliation. Lines (1-13) and LVED culture at passage 4 (P4) and passage (P16) are indicated at the left. Expression levels are indicated as follows: black boxes, very strong; dark gray, strong; light gray, detected; white, not detected.

DETAILED DESCRIPTION OF THE INVENTION

Figure 1:
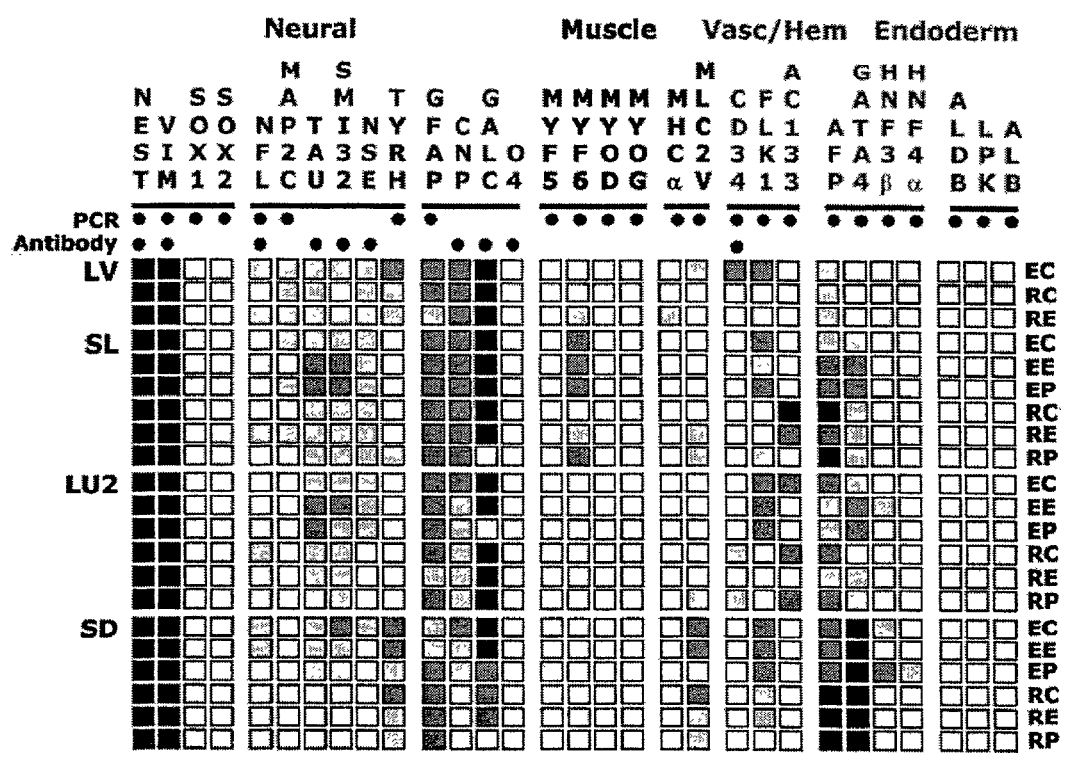
FIG. 1 shows the expression profiles of four EBD cultures. Markers and lineages are listed above and are grouped by lineage affiliation: neural, muscle, vascular/hematopoietic, and endoderm. The type of assay performed, whether PCR or antibody, is indicated by •. Culture identity is indicated at left LV, SL, LU2 and SD. The growth environment (combination of growth media and matrix) are indicated on the right as follows: E, EGM2MV media; R, RPMI/15% serum media; C, collagen I-coated surface; E, human extracellular matrix-coated surface; P, tissue culture-treated plastic surface. Expression levels are indicated as follows: black boxes, very strong; dark gray, strong; light gray, detected; white, not detected.

We have isolated cells from human embryoid bodies (EBs), termed "embroid body-derived (EBD) cells," that are capable of long-term and robust proliferation in culture.

Unlike EBs, which are large, multicellular three-dimensional structures, EBDs grow as a monolayer and can be continuously passaged. The in vitro proliferative capacity of EBD cells allows for routine genetic and epigenetic manipulation as well as clonal isolation. Furthermore, extended proliferation in an environment nonpermissive for EG cells also reduces the possibility of stem cell contamination. Although EBD cells are not immortal, they display long-term growth and proliferation in culture, e.g., a greater than about 30, about 40, about 50, about 60, about 70, about 80, or about 90 or more population doublings (PD). EBD cells proliferate in cell culture conditions that are non-permissive for growth of EG cells, reducing the risk of stem cell contamination. For example, EBD cells can be grown in culture media lacking leukemia inhibitory factor (LIF) or a fibroblast feeder layer.

Mixed cell EBD cultures and clonally isolated EBD cell lines simultaneously express a wide array of mRNA and protein markers that are normally associated with cells of multiple distinct developmental lineages, including neural (ectodermal), vascular/hematopoietic (mesodermal), muscle (mesodermal) and endoderm lineages. Mesodermal cells include, for example, connective tissue cells (e.g., fibroblasts) bone, cartilage (e.g., chondrocytes), muscle (e.g., myocytes), blood and blood vessels, lymphatic and lymphoid organs cells, neuronal cells, pleura, pericardium, kidney, gonad and peritoneum. Ectodermal cells include, for example, epidermal cells such as those of the nail, hair, glands of the skin, nervous system, the external organs (e.g., eyes and ears) and the mucosal membranes (e.g., mouth, nose, anus, vaginal). Endodermal cells include, e.g., those of the pharynx, respiratory tract, digestive tract, bladder, liver, pancreas and urethra cells. The terms "develop," "differentiate" and "mature" all refer to the progression of a cell from the stage of having the potential to differentiate into at least two or more different cellular lineages to becoming a specialized cell or a cell restricted in a developmental context. The growth and expression characteristics of EBD cells reveal an uncommitted precursor or progenitor cells phenotype.

The human EBD cell cultures of the invention simultaneously express various mRNA and polypeptides markers in a pattern atypical of naturally occurring cells. Thus, EBD cell cultures of the invention can be characterized by the presence or absence of particular markers, as discussed more fully in the Examples below. Such markers include the intermediate filament protein nestin, the neural epithelial marker vimentin, SOX-1, SOX-2, neurofilament light (NFL), microtubule associated protein-2C (MAP2C), TAU, the nerve cell cytoskeletal marker SMI32 neurofilament protein, neuron-specific enolase (NSE), tyrosine hydroxylase (TyrH), glial fibrillary acidic protein (GFAP), the myelin marker enzyme 2', 3' e.g.— cyclic nucleotide 3'-phosphodiesterase (CNP), galactocerebroside (GalC), the terminal oligodendrocyte marker (O4), a key basic Helix-Loop-Helix transcription factor capable of converting many non-muscle cells into muscle termed myogenic factor-5 (MYF5), the muscle determining gene myogenic factor-6 (MYF6), myogenic factor-D (MYOD), myogenic factor-G (MYOG), myosin heavy chain-α (MHC-α), myosin light chain-2v (MLC2V), CD34, VEGF receptor FLK1, stem cell marker AC 133, AFP, transcription factor GATA4, hepatic nuclear factor-3β (HNF3β), hepatic nuclear factor-4α (HNF4α), aldolase B (ALDB), LPK, and ALB. Not all markers will be present on all cells, e.g., some markers may be absent on some cells of a population of cells of the invention due to differences in developmental state, culture conditions, etc. All EBD cell cultures tested to date express an ectodermal marker, particularly nestin and vimentin, which are not expressed in ES and EG cells. In addition, all express a marker characteristic of at least one other cell lineage, i.e., a mesodermal and/or endodermal marker. In many cases, EBD mixed cell cultures or clonal cell cultures express an ectodermal, mesodermal and endodermal marker.

The growth environments that we have studied had a significant effect on the proliferation of EBD cells but did not predictably influence their gene expression profiles. This was not unexpected, as EBs are heterogeneous with respect to cell type content and the environments were designed to be generally supportive rather than specifically tailored to a particular cell type. This was substantiated by differences in EBD expression profiles when multiple cultures were initiated in parallel or serially from one EG culture. The strongest and most consistent antibody and PCR markers were markers associated with neural lineages. However, EBD cell cultures and clonal lines cannot be viewed simply as neural progenitors, as they simultaneously express markers from multiple, distinct cell lineages. Multilineage gene expression has been reported in other precursor or progenitor cell populations, but not with such a broad range.

Unlike EG cells and EBs, EBD cells can be cryopreserved by well-known techniques, including but not limited to, preserving in 10% dimethylsulfoxide (DMSO) in 20%-40% fetal bovine serum (FBS).

A further advantage of EBD cells for use in tissue transplantation therapy is that they do not cause teratocarcinoma to form when injected into immunocompromised severe combined immunodeficiency (SCID) mice.

The properties of EBD cells of the invention make them useful as models of human cell differentiation. In addition, EBD cells and cell cultures are useful in transplantation therapies for the treatment of such diseases, trauma, and injury as, for example, Parkinson's disease, amyotrophic lateral sclerosis (ALS), stroke, spinal cord injury, and diabetes. For some purposes, it may be advantageous to use non-clonal EBD cell cultures for purposes of transplantation therapy purposes, as such cultures comprise diverse cells that are morphologically distinct, express different markers, etc. However, clonal EBD cell lines may also be used. In order to assess the usefulness of a particular clonal EBD cell line for treatment of a disease, injury or trauma, it may be advantageous to screen or select various EBD cell lines for expression of genes that are expressed in the tissue that is affected by the disease, injury or trauma. For example, a population of EBD cells can be transformed with a polynucleotide construct comprising a promoter that is expressed in progenitors of a particular cell or tissue of interest and in the mature cell that that is operably linked to and drives the expression of a selectable marker, such as an antibiotic resistance gene. When challenged with selection pressure (e.g., by adding an antibiotic to the culture medium), surviving cells are those that express the selectable marker and thus are likely to develop into the type of cells that need to be replaced in order to treat the disease or repair the injury or trauma.

EBD cells can be used to study human embryological development. For example, EBD cells can be manipulated so as to express detectable markers such as green fluorescent protein (GFP), β-glucuronidase (GUS), β-galactosidase, etc.

Definitions

The term "AC133 polypeptide" refers to a protein expressed on, e.g., hematopoietic human stem cells, see, e.g., Buhring, *Blood* 94:832-823, 1999; Horn, *Blood* 93:1435-1437, 1999.

The term "CD34 polypeptide" refers to a protein expressed on, e.g., cells of hematopoietic origin (see, e.g., Steen, *Leuk. Lymphoma* 30:23-30, 1998; Holyoake, *Blood Rev.* 8:113-124, 1994).

The term "embryoid bodies" or "EBs" refers to collections of cells formed from the aggregation or clustering of cultured embryonic germ (EG) cells in culture, as described herein. EBs have a three dimensional morphology, e.g., they can be a solid or a cystic embryoid body.

The term "embryonic germ cells" or "EG cells" refers to cells isolated or derived from primordial germ cells (PGCs). EG cells include cells derived from PGCs and cultured as described herein, including cell lines derived from these EG cells and all progeny.

The term "primordial germ cells" (PGCs) refers to undifferentiated embryonic germ cells isolated from post-fertilization from anlagen or from yolk sac, mesenteries, or gonadal ridges of an embryo or a fetus. PGCs can be harvested from the mesenteric or genital ridges of embryos or as gonocytes of later testicular tissues. EG and PGC cells are described in further detail in U.S. Pat. No. 6,090,622.

The term "embryonic stem cells" or "ES cells" refers to cells that are derived from the inner cell masses of pre-implantation embryos.

The term "Relatively uncommitted" and "progenitor" and "pluripotent" refers to cells that retain the developmental potential to differentiate into a wide range of cell lineages, including the germ line.

The term "STO cell" refers to embryonic fibroblast mouse cells such as are commercially available and include those deposited as ATCC CRL 1503.

"Transplants" include cells (or parts thereof), cell products, tissue, or cell culture products grafted into a host.

"Transgene" means any piece of DNA inserted by artifice into a cell that becomes integrated into the genome of that cell (including cell line, tissue or organism). The transgene can be stably integrated or remain a stable extrachromosomal element. A transgene may include a gene that is partly or entirely heterologous (i.e., foreign) to the cell or organism to which the transgene is introduced. Alternatively, it may comprise a gene homologous to an endogenous gene of the recipient. Included within this definition is a transgene created by the providing of an RNA sequence that is transcribed into DNA and then incorporated into the genome.

The term "transgenic" includes any transgenic technology familiar to those in the art which can produce an organism, cell, cell culture, cell line, tissue or embryo carrying an introduced transgene or one in which an endogenous gene has been rendered nonfunctional or "knocked out." A "transgenic" is an animal or any part thereof, including, but not restricted, to cells, cultures or tissues which includes exogenous genetic material within its cells.

The term "gene knockout" as used herein, refers to the targeted disruption of a gene with either partial or complete loss of function achieved by any transgenic technology familiar to those in the art. For example, transgenic cells having gene knockouts are those in which the target gene has been rendered nonfunctional by an insertion targeted to the gene to be rendered nonfunctional by homologous recombination.

"Transfected" means a cell into which (or into an ancestor of which) has been introduced, by means of any recombinant nucleic acid techniques known to those in the art, a heterologous nucleic acid molecule. "Heterologous nucleic acid" refers to a nucleic acid sequence that either originates from another species or is modified from either its original form or the form primarily expressed in a cell.

Generating Embryoid Bodies (EBs) and Characterization of EBD Cells

Human embryoid bodies (EBs) form spontaneously in human PGC-derived stem cell cultures (see Example 1, below) that have been maintained in the presence of leukemia inhibitory factor (LIF) (e.g., human recombinant leukemia inhibitory factor) at about, e.g., 1000 units/ml, basic fibroblast growth factor (bFGF), at about 1 ngrn/ml, and forskolin at about 10 µM for greater than about one month, and, in some situations, as long as three to six months. EBs are also formed when these factors are withdrawn. Additional factors can be added to enhance or direct this process, including, but not limited to, retinoic acid, dimethylsulfoxide (DMSO), cAMP elevators such as forskolin, isobutylmethylxanthine, and dibutryl cAMP, cytokines such as basic fibroblast growth factor, epidermal growth factor, platelet derived growth factor (PDGF and PDGF-AA) nerve growth factor, T3, sonic hedgehog (Shh or N-Terminal fragment), ciliary neurotrophic factor (CNTF), erythropoeitin (EPO) and bone morphogenic factors.

Several cell types have been identified in human EBs through immunohistochemical and morphological analysis. These include muscle cells, vascular endothelial cells, neuroepithelial cells and visceral endoderm. Additionally, neuroepithelial cells and neuronal cells have been identified, along with the progenitor cells. Generation of EBs in culture and the harvesting and characterization of EBD cells are described in further detail in Examples 2 to 4, below.

Transformation and Infection of EBD Cells

EG cells used to generate EBs can be genetically manipulated before generation of the EB. However, EBD cells are susceptible to genetic manipulation by introduction of heterologous nucleic acid sequences to add to or alter their phenotype by standard human cell transformation techniques. For example, a transgene of interest may be introduced into an EBD cell of the invention by electroporation, calcium phosphate precipitation, microinjection, lipofection, transduction with retroviral, lentiviral or other viral or microbial vectors, or other means.

For example, the cells can be transiently or stably transfected with nucleic acids (including, e.g., various plasmids, vectors, recombinant viruses) encoding a polypeptide, e.g., a receptor, a ligand, a neurotransmitter, and the like genetic constructs are introduced into EBD cells by electroporation, calcium phosphate, microinjection, lipofection, retroviral or other viral (e.g., lentivirus, adenovirus, adeno-associated virus) or microbial vector or other well known means. The constructs can be designed not to integrate into a genome and/or stably propagate as an episome. Such constructs have a transient effect on cells. Alternatively, the constructs are allowed to incorporate stably into a genome.

The EBD cells of the invention can be manipulated with the same types of powerful experimental manipulation currently available with mouse ES and EG cells. In one aspect of the invention, stable genetic modifications allow gene replacement and repair through homologous recombination (see, e.g., Thomas, Cell 51:503-512, 1987; Capecchi, Science 244: 1288-1292, 1989; Doetschman, Nature 330:576-578, 1987). DNA constructs consisting of human DNA flanking the region to be replaced, repaired, augmented, or in any other way altered, along with DNA which contains the altered region and DNA which codes for positive and negative drug selection expression cassettes is transferred to the cell. DNA constructs containing normal or modified human genes or chromosomal regions, or combinations of human, other animal, and wholly artificial genes, along with genetic elements that allow propagation in a suitable bacterial, yeast or animal cell host are transferred to cells of the invention. Cells in which the DNA construct(s) have integrated into a genome or are stably maintained as an episome are detected using standard techniques such as Southern blotting and polymerase chain reaction (PCR). Expression systems that can be used include cosmids, bacteriophages, plasmids and viral or retroviral vectors (see, e.g., Walther, Drugs 60:249-271, 2000).

Exemplary viral and retroviral systems that can be used to genetically modify the cells of the invention include, e.g., adenovirus-based vectors (see, e.g., Wickham, Gene Ther. 7:110-114, 2000; U.S. Pat. Nos. 6,136,594, 5,670,488 and 5,670,488), Epstein-Barr virus-based vectors (see, e.g., Mazda, J. Immunol. Methods 204:143-151, 1997; U.S. Pat. No. 4,997,764), adenovirus-associated virus (AAV) vectors (see, e.g., U.S. Pat. Nos. 5,622,856 and 5,856,1520; Sindbis virus vectors (see, e.g., Strong, Gene Ther. 4:624-627, 1997; U.S. Pat. Nos. 6,136,538 and 5,843,712), Herpes simplex virus vectors (see, e.g., Kennedy, Brain 120:1245-1259, 1997; U.S. Pat. Nos. 6,106,826 and 6,071,692); lentivirus vectors (see, e.g., Barrette, Blood 96:3385-3391, 2000; U.S. Pat. Nos. 6,096,538, 5,804,196 and 5,631,154) and retroviral vectors (see, e.g., Miranda, Gene Ther. 7:1768-1776, 2000; U.S. Pat. Nos. 6,140,111, 6,132,962, 6,107,478, and 6,096,538).

Other systems that can be used to add homologous or heterologous DNA to a genome include various artificial chromosomes, e.g., yeast artificial chromosomes (YAC), bacterial artificial chromosomes (BAC), P1 derived artificial chromosomes (PAC), human artificial chromosomes (HACs) and the like. For example, yeast artificial chromosome (YAC) can mediate insertion of a portion of human chromosome 21 into mouse ES cells, see, e.g., Lamb Nature Genetics 5:22-30, 1993). Human artificial chromosomes (HACs) constructed of alpha satellite DNA, telomeric DNA, and genomic DNA can be introduced into cells.

In another embodiment and use of the invention, cells of the invention are genetically manipulated with constructs comprised of reporter molecules such as β-galactosidase, luciferase, or chloramphenicol acetyl transferase (CAT). These constructs can include tissue-or developmental-specific promoters, so that aspects of differentiation can be studied. Random integration of promoter- or enhancerless reporter constructs into a genome followed by differentiation can allow discovery of new human gene promoters and enhancers. Reporter constructs with tissue- or development specific, or constitutive promoters can be used to trace the integration and survival of implanted cells.

Human EBD cells of the invention that have been altered by stable introduction of a transgene can be used individually (e.g., to generate clones or EBs) or to generate tissue-engineered tissues or organs. These cells can be administered to subjects in the treatment of various disorders to enhance, add or diminish the expression of a desired gene. These cells can be used to identify compounds and small molecules that interact with the genetically modified or unmodified cells.

In one aspect, the invention provides EBD cells having one or more genetic modifications for, e.g., providing modified cells for gene therapy or replacement tissues for grafting or implantation (e.g., to avoid host rejection of the cells). This application can be used to model or treat contiguous gene disorders, aneuploidy or other large-scale chromosomal phenomenon. In another embodiment and use of the invention, multiple changes are made to an EBD genome, e.g., by serial transgenic events using different drug selection genes in each construct, followed by appropriate drug selection of the cells.

The invention also provides for large-scale genetic manipulation of EBD cell genomes. Large (3 to 4 cM) chromosomal regions can be deleted, inverted, translocated, or duplicated using, e.g., cre/loxP mediated chromosome engineering (see, e.g., Ramirez-Solis, Nature 378:720-724, 1995). Homologous recombination or random insertional transgenesis techniques can be used to serially integrate small genetic elements termed loxP sites into an EG cell genome. The cells are then treated with cre protein administered by lipofection or transient transfection. The EG cells can then be maintained in an undifferentiated state or allowed to differentiate as described below. Tissue- and developmental-specific expression of cre can be accomplished using this technique.

Cell Culture of EG Cells, EBs and EBD Cells

The invention provides for the culturing of EG and EB cells to form EBDs of the invention and the culturing of EBD cells and cell lines. EBD cells can be clonally isolated and are capable of robust and long-term proliferation in culture.

EBD cells are grown and maintained in culture medium or growth medium. Examples of suitable culture media useful in practicing the present invention include a variety of growth media prepared with various base media, such as Dulbecco's minimal essential media (DMEM) supplemented with serum. Examples of such serum include fetal bovine serum (FBS) and fetal calf serum (FCS). Serum may be provided in a concentration of between about 1% and about 25%, between about 2.5% and about 20% or at about 15%. Other substituents can also be included, such as, 2 mM glutamine, 1 mM sodium pyruvate, or glucose and phosphate free modified human tubal fluid media (HTF) supplemented with 15% fetal calf serum, 0.2 mM glutamine, 0.5 mM taurine, and 0.01 mM each of the following amino acids asparagine, glycine, glutamic acid, cysteine, lysine, proline, serine, histidine, and aspartic acid (see, e.g., McKieman 421:88-199, 1995). EG medium can also contain commonly used tissue culture antibiotics, such as penicillin and streptomycin. A variety of commercial media can be adapted for use with the invention, e.g., Clonetics (Walkersville, Md.), EGM2MV™ media; BD Biosciences (San Jose, Calif.) Hepatostim™ media. "Conditioned medium" refers to a growth medium that is further supplemented by factors derived from media obtained from cultures of feeder cells on which EG or EBD cells can be cultured. An effective amount of factors can be added, e.g., periodically, e.g., daily, to either of these base solutions to prepare human EG growth media. The term "effective amount" as used herein is the amount of such described factor as to permit a beneficial effect on human EG growth and viability of human EG cells using judgment common to those of skill in the art of cell culturing and by the teachings supplied herein.

"Growth factor" as used for the purposes of describing the present invention refers to a substance that is effective to promote the growth of EG or EBD cells that is not otherwise a component of the growth medium. Such substances include, but are not limited to, cytokines, chemokines, small molecules, neutralizing antibodies, and proteins. Growth factors also include intercellular signaling polypeptides that control both the development and maintenance of cells, and the form and function of tissues. "Non-essential Amino acids" refers to the amino acids L-alanine, L-asparagine, L-aspartic acid, L-glutamic acid, glycine, L-proline, and L-serine. Cell culture media may also include a reducing agent.

The EBD cells may be dependent on some growth factors for maintenance in the cultured state. In one embodiment the growth factor is human basic fibroblast growth factor (bFGF). A growth factor may also be provided to assist in the derivation and maintenance of cultures of EBD cells in a substantially undifferentiated state. The identities and effective concentrations of such growth factors can be determined using the methods as described herein or using techniques known to those of skill in the art of culturing cells. For example, one or more of the following factors can be used at the stated final concentration: forskolin ([3R-(3α, 4αβ, 5β, 6β, 6αα, 10α, 10αβ, 10bα)]-5-(acetyloxy)-3-ethenyldodecahydro-6, 10, 10β-trihydroxy-3, 4 α, 7, 7, 10 α-pentamethyl-1H-naphtho [2, 1-b]pyran-1-one) at 10 μM, cholera toxin at 10 μM, isobutylmethylxanthine (IBMX) at 0.1 mM, dibutyladenosine cyclic monophosphate (dbcAMP) at 1 mM. In another embodiment, the growth factor is basic fibroblast growth factor (bFGF), more specifically, human recombinant basic fibroblast growth factor (bFGF), in the range of about 1-10 ng/ml.

The EG or EBD cells can be grown on a plate in addition to the feeder cells. Alternatively, the feeder cells can be first grown to confluence and then mitotically inactivated (e.g., by irradiation) to prevent further growth. Such an approach has the advantage of simplifying the management of the cell culture as the growth of only one set of cells, the EG cells, need only be monitored.

Another factor is growth media harvested from cultures of human embryonal carcinoma (EC) cells. For example, human NTERA-2 EC cells (ATCC accession number CRL 1973) are grown to confluence in DMEM supplemented with 10% fetal calf serum or mouse ES cells are grown to confluence in DMEM supplemented with 15% fetal calf serum, 2 mM glutamine, 1000 U/ml LIF. Growth media is harvested daily over several days, passed through a 0.22 micron filter and frozen at −80° C. This human EC or mouse ES "conditioned" media is added to the EG or EBD cell growth media in empirically determined amounts, as judged by the effect on EG or EBD cell growth and viability.

Once established, EBD cells can be cultured using a variety of techniques. In one example, a container holds feeder cells in a non-conditioned medium. A matrix of lysed feeder cells is prepared using standard methods. The cells to be cultured are then added atop the matrix along with the conditioned medium. Alternatively, the EBD cells can be grown on living feeder cells using methods known in the art. The growth of the EG cells is then monitored to determine the degree to which the cultured cells have become differentiated. A marker for alkaline phosphatase can be used to ascertain which cells have differentiated. When a sufficient number of cells have differentiated, or when the culture has grown to confluence, at least a portion of the undifferentiated cells can be passaged. The determination to passage the cells and the techniques for accomplishing such passaging can be performed using standard techniques well known in the art.

Embryonic Germ (EG) Cells and Methods of Culture

EG cells can be generated and cultured essentially as described in U.S. Pat. No. 6,090,622. The starting material for isolating cultured embryonic germ (EG) cells is tissues and organs comprising primordial germ cells (PGCs). For example, PGCs may be isolated over a period of about 3 to 13 weeks post-fertilization (e.g., about 9 weeks to about 11 weeks from the last menstrual period) from embryonic yolk sac, mesenteries, gonadal anlagen, or genital ridges from a human embryo or fetus. Alternatively, gonocytes of later testicular stages can also provide PGCs. In one embodiment, the PGCs are cultured on mitotically inactivated fibroblast cells (e.g., STO cells) under conditions effective to derive EGs. The resulting human EG cells resemble murine ES or EG cells in morphology and in biochemical histotype. The resulting human EG cells can be passaged and maintained for at least several months in culture.

In culturing EG cells, it is believed that the use of feeder cells, or an extracellular matrix derived from feeder cells, provides one or more substances necessary to promote the growth of EG cells and/or prevents or inhibits the rate of differentiation of such cells. Such substances are believed to include membrane-bound and/or soluble cell products that are secreted into the surrounding medium by the cells. For example, EG cells can be grown on a substrate consisting of mouse embryo fibroblast cells, STO cells, human fibroblasts, or human epithelium cells. Thus, those of skill in the art will recognize that additional cell lines can be used with the cell culture medium to equivalent effect and that such additional cell lines can be identified using standard methods and materials. In addition, those of skill in the art will also recognize that one or more substances produced by the feeder cells, or contained in the extracellular matrix, can be identified and added to the cell culture medium to obviate the need for such feeder cells and/or such extracellular matrix. Such feeder cells are not needed for proliferation of EBD cells in culture, however.

Production of Long-Lived Cells by Telomerase Transfection

Although human EBD cells of the invention express telomerase activity, it may be desirable to enhance such expression to increase the lifespan of the cell. This can be effected by increasing the activity of endogenous telomerase or by transfection with an exogenous telomerase-expressing construct. Alternatively, it may be desirable to produce EBD cells whose telomerase activity induced or suppressed under controlled conditions. Thus, the present invention includes EBD cells transfected with telomerase-expressing constructs as well as cells derived from such transfected cells (see, e.g., U.S. Pat. No. 6,093,809; WO 98/14592; WO 00/46355). The present invention further includes EBD cells transfected with an inducible or suppressible telomerase (see, e.g., U.S. Pat. Nos. 5,863,726; 6,054,575). EBD cells that have been transfected with telomerase can be propagated in vitro for greater than 100 PD.

All normal somatic living cells exhibit the Hayflick limit, that is, a finite number of replications after which the cells enter a senescent, nondividing phase. The Hayflick limit results from progressive shortening of telomere lengths (chromosome tips) with each replicative division. The enzyme telomerase has been shown to restore the length of telomeres when transfected into normal dividing cells and extends their replicative lifespan indefinitely without causing malignant transformation (see, e.g., Bodnar, *Science* 279: 349-352, 1998). This technology enables one to increase the lifespan or to immortalize a cell without altering its normal physiology.

In another aspect, the determination of endogenous or genetically implanted telomerase activity EBD cells and their differentiated derivatives are used to determine their longevity and engraftment potential. EBD cells cultured using the methods and materials of the invention are stably transfected to express the components of telomerase and allowed to differentiate, or, alternatively, induced to differentiate, to produce progenitor or pluripotent daughter cells such as hematopoietic stem cells for use in transplantation. Induction of differentiation can be performed as described herein, including using agents effective to induce differentiation, such as retinoic acid. The cells may carry additional genetic modifications using the methods herein. Cells identified as having strong telomerase expression can be specifically isolated and used for transplantation, further culturing, generation of engineered tissues and organs, and other modification as described herein.

Screens for Culture Media Factors

In another embodiment and use of the invention, EBD cells are used to optimize the in vitro growth and culture conditions for maintaining an undifferentiated state, or, for differentiating the cells. High-throughput screens can be established to assess the effects of media components, exogenous growth factors, and attachment substrates. These substrates include viable cell feeder layers, cell extracts, defined extracellular matrix components, substrates which promote three-dimensional growth such as methylcellulose and collagen, novel cell attachment molecules, and/or matrices with growth factors or other signaling molecules embedded within them. This last approach may provide the spatial organization required for replication of complex organ architecture (as reviewed in Saltzman, *Nature Medicine* 4:272-273, 1998).

A variety of components can be measured to quantify the effects of the experimental treatment. These include the alkaline phosphatase activity of undifferentiated cells, substances produced by differentiating or differentiated derivatives, or reporter molecules. EG and the EBD cells and derivatives gradually adapt to convenient or experimentally essential growth conditions, such as a reduced requirement for LJF and feeder layers. This allows the testing of dissociation enzymes that allow efficient passage but do not destroy essential cell surface molecules.

The presence of increased alkaline phosphatase activity can indicate that the substance being tested is a growth factor. The level of expression of alkaline phosphatase can be determined for each group of cells exposed to a particular putative growth factor and correlated with increased alkaline phosphatase expression relative to control cells not exposed to a putative growth factor. In one embodiment, substances found to produce an increase of alkaline phosphatase expression greater than about 20% as compared with the control are considered growth factors. Substances identified as growth factors screen can be tested in a secondary screen to determine the presence or absence of a correlation between exposure of the cells to the substance and a parallel increase in the expression of surface markers associated with non-differentiation such as SSEA-4, SSEA-3, TRA-1-60 (ATCC HB-4783) and TRA-1-81 (ATCC HB-4784), and/or the expression of telomerase. The cells are cultured as described herein. The cells are then exposed to an antibody raised against one or more of the surface markers being screened, and/or the presence or absence of telomerase expression in the exposed cells is determined (see, e.g., U.S. Pat. Nos. 5,863,726; 5,989,807). In some embodiments, the surface marker antibodies are incubated with a second antibody coupled with a reporter such as a fluorescent label so that cells expressing the appropriate antigenic marker are rendered fluorescent. Labeled cells can then be sorted and counted using standard methods, e.g., a fluorescence-activated cell sorter (FACS). The numbers of labeled and unlabeled cells can then be compared to determine the effect of the putative growth factor. Alternatively, following exposure to unlabeled cell surface marker antibodies, the cells are exposed to a second antibody that is specific for the cell surface marker antibody in an ELISA format from which the number of cells expressing the desired surface antigen can be quantitated calorimetrically or by measurement of fluorescence. Those substances confirmed to be growth factors can also be tested in combination (e.g., combinations of two or three substances) to determine the presence of any synergistic properties among the growth factors. In addition, substances that may promote differentiation or retard the growth of undifferentiated cells can be identified. For example, antibodies directed to substances in the growth medium can be added to prevent those substances from interacting with the cells being cultured.

Controlled Differentiation of Human EBD Cells

The EBD cells of the invention can differentiate in vitro into a wide variety of cell and tissue types, including embryonic and more highly differentiated cells and specialized structures. For example, to induce differentiation in monolayer cultures, EBD cells are cultured for two weeks without passage onto a fresh feeder layer. To induce differentiation in suspension culture, the cells are passed onto a gelatinized plate to eliminate possible contamination by fibroblasts. After 4 to 7 days in culture, colonies are gently dislodged from the plate and disaggregated after incubation in 0.25% trypsin-EDTA for 10-15 min. Dissociated cells are cultured in a microdrop of culture medium containing 0.3 µM retinoic acid on a 35-mm non-adhesive petri dish. Suspension cultures are monitored daily for embryoid body formation which is indicative of a differentiated phenotype. Similar experiments testing for differentiation of attached cells are well known to those in the art.

The EBD cells of the invention can be differentiated into various more differentiated cell types, some of which are listed herein. A broadly applicable method of obtaining pure populations of specific cell types during EBD cell differentiation involves the use of a cell-type specific promoter driving a selectable marker gene, e.g., one providing resistance to an otherwise toxic drug. Under the appropriate differentiation conditions, in the presence of the drug, only those cells that can activate the selectable marker (those undergoing the desired differentiation) survive.

Generation of Neuroepithelial Cells

In one aspect of the invention, the EBD cells and cell lines are differentiated to generate neuroepithelial cells. These cells can be used, e.g., to augment or replace cells damaged by illness, autoimmune disorders, accidental damage, or genetic disorder. EBD cells of the invention can be induced to differentiate in vitro with retinoic acid to form neuronal and glial precursors, positive for astrocyte (GFAP) or oligodendrocyte (O4) markers, then later into functional neurons (see, e.g., Fraichard, *J. Cell Science* 108:3161-3188, 1995). Cells transplanted to adult brains were observed innervating the host striatum (Deacon, *Exp. Neurology,* 14928-41, 1998). As with human and mouse EC cell lines, EBD cells of the invention can be induced to differentiate into neurons, see, e.g., Trojanowski, *Exp. Neurology* 144:92-97, 1997; Wojcik, *Proc. Natl. Acad. Sci. USA* 90:1305-1309, 1993. Transplantation of neurons generated by these methods into rats subjected to cerebral ischemia promoted a degree of functional recovery, see Borlongan, Exp. *Neurology* 149:310-321, 1998.

Expression of the SV40 T antigen (Tag) may allow proliferation of neuroepithelial precursor cells, and that normal differentiation can resume upon repression of Tag (see, e.g., Lei, *Mol. Endocrinol.* 6:703-712, 1992; Lew, *Genes Dev.* 7:683-693, 1993; Alarid, *Development* 122:3319-3329, 1996). The use of inducible expression systems (e.g., the tetracycline-inducible promoter system) or specific deletion of the over-expression construct through a Cre/lox recombination event would allow resumption of the normal differentiation sequence after appropriate expansion of the neuroepithelial precursors.

The present invention provides for the modification and/or differentiation of EBD cells for the production of neuronal stem cells using the gene modification techniques and strategies, e.g., as those described above. Two overlapping strategies can be used to obtain expanded populations of neuroepithelial precursor cells: (1) the use of culture conditions effective to induce neuroepithelial precursor cell formation from undifferentiated cells of the invention, and (2) genetic approaches to increasing the yield of neuroepithelial precursors.

In one embodiment, the present invention provides methods and materials to produce neuroepithelial stem cells from EBD cells. Embryoid bodies are replated in insulin-transferrin-selenium-fibronectin (ITSN) supplemented medium, a medium that is effective in inducing neuronal differentiation in embryonal carcinoma cells (Rizzino, *Proc. Natl. Acad. Sci. USA* 77:457-461, 1980). These cells are cultured for 6 to 7 days in the same medium, dissociated and re-plated into medium containing basic fibroblast growth factor (bFGF). Upon removal of FGF, neurons, astrocytes, and oligodendrocytes are expected to form in situ.

The ability to transfect undifferentiated embryonic stem cells also permits a genetic approach to neuroepithelial precursor cell derivation and expansion. As described previously, the use of cell-type specific promoters driving drug resistance genes allows the selection of specialized cells during cell differentiation. Accordingly, if the undifferentiated EBD cells are stably transfected with a selectable marker, such as a nestin promoter/near construct, the use of the culture conditions described above combined with drug selection can provide a significant enrichment for neuroepithelial cell precursors.

Generation of Hematopoietic Progenitor Cells

EBD cells and cell lines of the invention can also be used to generate hematopoietic progenitor cells (see, e.g., Rich, *Blood* 86:463-472, 1995). These EBD hematopoietic cells can be used to augment or replace cells damaged by illness, genetic disorder, or as an alternative to the use of bone marrow transplantation when indicated. EBD cells of the invention can be used to form blood islands capable of the generation of lymphoid and myeloid mixed-cell populations (see, e.g., Doetschman, *J. Embryol. Exp. Morph.* 87:27-45, 1985; Chen, *Proc. Natl. Acad. Sci. USA* 89:2541-2545, 1992). The in vitro derivation of hematopoietic cells can be enhanced by addition of stem cell factor (SCF), IL-3, IL-6, IL-11, GM, CSF, EPO, M-CSF, G-CSF and/or LIF to recapitulate hematopoietic development (see, e.g.; Keller, *Mol. Cell Biol.* 13:473-486, 1993; Kennedy, *Nature* 386:488-493, 1997; Biesecker, *Exp. Hematology* 21:774-778, 1993). The EBD cells of the invention can also generate hematopoietic stem cells, characterized as thyl+, SCA-I+, c-kit receptor+, lineage restricted marker negative, B-220, Mac-1, TEN 119, JORO 75 for B-lymphocyte, myeloid, erythroid, T-lymphocyte, respectively, when cultured on a stromal cell line in the presence of IL-3, IL-6 and fetal liver stromal cell line cultured supernatant. In vitro hematopoiesis also can be stimulated by over-expression of HOXB4 (Palacios, *Proc. Natl. Acad. Sci. USA,* 92:7530-7534, 1995). Using similar methods, EBD cells of the invention can be induced to differentiate and form hematopoietic progenitor cells.

Generation of Cardiomyocytes

The invention also provides cardiomyocytes generated from the EBD cells of the invention. EBD cells of the invention can be induced to differentiate in vitro to form cardiomyocytes (see, e.g., Wobus, *Differentiation* 48:173-182, 1991; Maltsev, *Mech. Dev.* 44:41-50, 1993; Klug, *J. Clin. Invest.* 98:216-224, 1996). Cardiomyocytes generated from murine ES cells expressed appropriate cardiac-specific genes including sarcomeric myosin, desmin, myosin heavy chain, and dystrophin. The cells were electrically coupled and showed action potentials typical of atrial, ventricular, and sinus node cardiomyocytes. These cardiomyocytes exhibited spontaneous and rhythmic contractions for as long as 11 months in culture (see Klug, *J. Clin. Invest.* 98:216-224, 1996). It can be expected to see spontaneous formation of cardiomyocytes from EBD cells of the invention.

EBD cells of the invention can be maintained in the undifferentiated state, as described herein. Using the methods and materials described herein, conditions can be determined to induce substantially specific differentiation of the EBD cells of the invention into cardiomyocytes. In one embodiment, to generate cardiomyocytes, EG cells are detached from feeder layers and plated in suspension in bacteriological culture plates in typical culture medium in the absence of leukemia inhibitory factor. Under such conditions, the cells form the three-dimensional-structured EBs of the invention and begin to demonstrate the formation of multiple differentiated cell types. Because EG cells require feeder layers for growth, it may be advantageous to first allow extensive overgrowth of the EG cells on the feeder layers to form three-dimensional structures analogous to EBs, then trypsinize and re-plate to obtain larger yields of cardiomyocytes. After 3 to 7 days growth in suspension, the embryoid bodies are re-plated onto typical tissue culture dishes and allowed to attach. Spontaneously contracting regions are readily identified and can be isolated, dissociated, and re-plated. In the murine system, these techniques resulted in an overall cardiomyocyte yield of 3% to 4% (see Klug, *J. Clin. Invest.* 98:216-224, 1996).

Cardiomyocytes generated from EBD cells can be purified further by the use of cardiomyocyte specific promoters driving a selectable marker, e.g., the α-cardiac myosin heavy chain (MHC) promoter fused to the aminoglycoside phosphotransferase (neomycin resistance) gene. Undifferentiated EBD cells can be transfected with the α-MHC/neor construct. Plating onto tissue culture dishes will be in the presence of the drug G418. Under these conditions essentially pure populations of cardiomyocytes can be isolated (Klug (1996) supra). Given the ability to modify by transfection and expand undifferentiated EBD cells, large quantities of pure, fully functional cardiomyocytes can be derived. In addition, distinct types of cardiomyocytes show different patterns of gene expression. For example, myosin light chain (MLC) 2a is expressed in atrial but not ventricular cardiomyocytes; MLC-2v has the complementary pattern of expression (see, e.g., Klug, 1996, supra). The use of a subtype-specific promoter driving a selectable marker gene can allow the isolation of pure populations of specific cardiomyocytes.

Generation of Skeletal Muscle Cells

In another aspect, skeletal muscle cells can be generated from the EBD cells and cell lines of the invention. EBD cells and cell lines of the invention can be induced to differentiate into skeletal muscle in the presence of about $10^{-8}$ to $10^{-7}$ M retinoic acid (see, e.g., Wobus, *Roux's Arch. Dev. Biol.* 204: 36-45, 1994). The application of such conditions to EBD cell culture allows generation of skeletal muscle.

Alternatively, stably transfected undifferentiated EG or EBD cells comprising an inducible MyoD1 construct can be made. MyoD1 is a basic helix-loop-helix protein that has the ability to induce muscle gene expression in a variety of cell types (see, e.g., Weintraub, *Proc. Natl. Acad. Sci USA* 86:5434-5438, 1989). It has been demonstrated that transfection of murine ES cells with MyoD1, coupled with culture as embryoid bodies in the presence of DMSO, results in efficient formation of skeletal muscle (see, e.g., Dinsmore, *Cell Transplant* 5:131-143, 1996). Thus, induction of skeletal muscle by retinoic acid or the formation of human EBD cells comprising an inducible MyoD1 construct allows the growth of large quantities of skeletal myocytes. These cells can also be grown in co-culture with neurons generated from the EBD cells of the invention, as described above, to provide neuromuscular junctions.

Generation of Neuronal Networks

EBD cells and cell lines of the invention can also be used to generate neuronal networks using methods analogous to those used to generate networks from dissociated mouse embryos. Mouse neural networks were created on microelectrode arrays; these networks showed coordinated and quasi-periodic tiring patterns that responded to the presence of pharmacological agents by altering both the amplitude and the frequency of the burst patterns (see, e.g., Gopal, *Acta Otolaryngol.* 116:690-696:697-704, 1996). It is expected that EBD cells and cell lines of the invention can also form both excitatory and inhibitory synapses in culture; in mice, these synapses formed spontaneously upon differentiation (see, e.g., Finley, *J. Neurosci.* 161056-1065, 1996). The higher the density, the more frequent the likelihood of synapse formation.

Neurons generated from the EBD cells and cell lines of the invention can be coupled with microelectrode arrays using standard methods and materials. These neuronal cells are expected to form functioning neural networks. Such networks can be used to screen for pharmacological agents, the study of genetic conditions (using, for example, genetically modified EBD cells, as described above) and disease states.

Generation of Neuromuscular Junctions

The EBD cells and cell lines of the invention can also be used to generate neuromuscular junctions. Neuromuscular junctions are specialized synapses connecting nerves and muscles. They are the target of chemical and biological toxins; e.g., inhibitors of the enzyme acetylcholinesterase, which is normally responsible for the degradation of the neurotransmitter acetylcholine, thereby attenuating the stimulation of the muscle by the nerve. The cells of the neuromuscular junction exhibit measurable electrical membrane potentials and depolarization events that are extremely sensitive to perturbations in their micro-environments. Using the EBD cells and cell lines of the invention, neuromuscular junctions that are anatomically uniform can be produced in constant supply without any substantial drift in performance characteristics or sensitivity. Because they are of human origin, they represent the appropriate distribution of membrane receptors and biological response patterns characteristic of human beings. In one exemplary method, the skeletal myocytes generated from EBD cells are co-cultured with neurons generated from EBD cells of the invention. Thus, EBD cells of the invention can be used to generate neuromuscular junctions that can be used, inter alia, to detect toxins, study diseases, and screen for drugs.

Biosensors and Methods of Screening

EBD cells or cell lines of the invention and cells, tissues, structures and organs derived from them can be used for toxicological, mutagenic, and/or teratogenic in vitro tests and as biosensors. Thus, the invention provides engineered cells, tissues and organs for screening methods to replace animal models and form novel human cell-based tests. These systems are useful as extreme environment biosensors. EBD cells or cell lines of the invention and cells, tissues, structures and organs derived from them can be used to build physiological biosensors; for example, they can be incorporated in known system, as described, e.g., in U.S. Pat. Nos. 6,130,037; 6,129,896; and 6,127,129. These sensors can be implanted bio-electronic devices that function as in vivo monitors of metabolism and other biological functions, or as an interface between human and computer.

The invention also provides a method for identifying a compound that modulates an EB or an EBD cell function in some way (e.g., modulates differentiation, cell proliferation, production of factors or other proteins, gene expression). The method includes: (a) incubating components comprising the compound and EB or an EBD cell(s) under conditions sufficient to allow the components to interact; and (b) determining the effect of the compound on the EB or an EBD cell(s) before and after incubating in the presence of the compound. Compounds that affect EB or an EBD cell function include peptides, peptidomimetics, polypeptides, chemical compounds and biologic agents. Differentiation, gene expression, cell membrane permeability, proliferation and the like can be determined by methods commonly used in the art. The term "modulation" refers to inhibition, augmentation, or stimulation of a particular cell function.

Incubating includes conditions that allow contact between the test compound and the EB or an EBD cell. Contacting can be done under both in vitro and in vivo conditions. For example, it may be desirable to test an array of compounds or small molecules on a single or few EBs or EBD cells on a "biochip" or other solid support (see, e.g., U.S. Pat. No. 6,127,129). For example, cardiomyocytes or neurons on chips would give a readout of the rate of contraction or number of firings, respectively, in response to a compound and for the detection of harmful or at least biologically active environmental agents.

Neuronal biologically compatible electrode arrays allow the stem cells to undergo further differentiation on the array itself. These arrays allow the measurement of real time changes in electrical activity in the EBD neurons in response to the presence of known or unidentified agents. The electrical activity of cardiomyocytes can be monitored by plating the cells on an array of extracellular microelectrodes (see, e.g., Connolly, *Biosens. Biores.* 5:223-234, 1990). The cells show regular contractions, and the extracellular signal recorded showed a relationship to intracellular voltage recordings (Connolly, 1990, supra). This noninvasive method allows long term monitoring and is simpler and more robust than typical whole cell patch clamp techniques.

The test compound may optionally be a combinatorial library for screening a plurality of compounds. Compounds identified in the method of the invention can be further evaluated, detected, cloned, sequenced, and the like, either in solution or after binding to a solid support, by any method usually applied to the detection of a specific DNA sequence such as PCR, oligomer restriction (see, e.g., Saiki, *Bio/Technology* 3:1008-1012, 1985), allele-specific oligonucleotide (ASO) probe analysis (see, e.g., Conner et al. *Proc. Natl. Acad. Sci. USA* 80:278, 1983), oligonucleotide ligation assays (OLAs) (see, e.g., Landegren *Science* 241:1077, 1988), and the like.

In another aspect, cells cultured or modified using the materials and methods provided by the present invention are mounted to support surfaces to screen for bioactive substances. In one example, the cells are coupled with a substrate such that electrophysiological changes in the cells in response to external stimuli can be measured, e.g., for use as a high-throughput screen for bioactive substances. The cells can be transfected with DNA that targets, expresses, or knocks-out specific genes or gene products in the cell. By providing such chip-mounted cells coupled with measuring devices, such as a computer, many compounds can be screened rapidly and accurately. The biosensor could also be coupled to the measuring device in arrays for large-scale parallel screening.

The biosensor provided by the present invention can also be used to screen for, or warn of, environmental toxins or exposure to dangerous chemicals. In one embodiment, the above-described biosensor is exposed to environmental substances (e.g., air, water, soil), or to samples derived therefrom, and the response of the biosensor is monitored. If a dangerous agent is detected, the response of the system to the agent can be recorded for evaluation, a portion of the sample can be isolated for further study, and an alarm sounded.

Disease Models Using EBD Cells

The invention also provides in vitro models for human genetic diseases using the EBD cells of the invention, including their differentiated forms. If desired, genetic manipulations can made to these cells to influence differentiation, cell physiology, growth rate, etc. These cells can also be used for the study of polygenic and contiguous gene disorders, where large-scale or serial manipulations are required. One example of this is the study of human globinopathies by introduction of mutation(s) and study the cells as they differentiate into hematopoietic cells. Other examples are the study of muscular defects and neuronal defects.

Transplantation of EBD Cells

The invention also provides unmodified or genetically modified EBD cells or their differentiated progeny for use in human transplantations in the fetus, newborns, infants, children, and/or adults.

One example of this use is therapeutic supplementation of metabolic enzymes for the treatment of autosomal recessive disorders. For example, production of homogentisic acid oxidase by transplanted EBD differentiated cells into the liver could be used in the treatment of alkaptonuria (for review of this disorder, see McKusick, Heritable Disorders of Connective Tissue. 4th ed., St. Louis, C. V. Mosby Co., 1972). Likewise, ornithine transcarbamylase expression could be augmented to treat the disease caused by its deficiency. In another example, glucose-6-phosphate dehydrogenase expression could be augmented in erythrocyte precursors or hematopoietic precursors to allow expression in red blood cells in order to treat G6PD deficiency (favism, acute hemolytic anemia).

Treatments of some diseases require addition of a composition or the production of a circulating factor. One example is the production of $\alpha$1-antitrypsin in plasma to treat a deficiency that causes lung destruction, especially in tobacco smokers. Other examples of providing circulating factors are the production of hormones, growth factors, blood proteins, and homeostatic regulators.

In another use of the invention, EBD cells or their differentiated derivatives are used to repair or supplement damaged or degenerating tissues or organs. This may require that the cells are first differentiated in vitro into lineage-restricted stem cells or terminally differentiated cells. One example of this is differentiation of EG into vascular cells and channels, then used to repair or create veins and arteries. Mouse ES cell embryoid bodies have been shown to form vascular channels (see, e.g., Wang, *Development* 114:303-316, 1992), and this in vitro development can be enhanced with angiogenic factors (Doetschman, *Hypertension* 22:618-629, 1993). Parkinson's disease can be ameliorated by transplantation of EBD differentiated cells producing appropriate amounts of dopamine (see, e.g., Bohn, *Mol. Ther.* 1:494-496, 2000).

Before implantation or transplantation the EBD cell can be genetically manipulated to reduce or remove cell-surface molecules responsible for transplantation rejection in order to generate universal donor cells. For example, the mouse Class I histocompatibility (MHC) genes can be disabled by targeted deletion or disruption of the $\beta$-microglobulin gene (see, e.g., Zijlstra, *Nature* 342:435-438, 1989). This significantly improves renal function in mouse kidney allografts (see, e.g., Coffinan, *J. Immunol.* 151:425-435, 1993) and allows indefinite survival of murine pancreatic islet allografts (see, e.g., Markmann, *Transplantation* 54:1085-1089, 1992). Deletion of the Class II MHC genes (see, e.g., Cosgrove, *Cell* 66:1051-1066, 1991) further improves the outcome of transplantation. The molecules TAP1 and Ii direct the intercellular trafficking of MHC class I and class II molecules, respectively (see, e.g., Toume, *Proc. Natl. Acad. Sci. USA* 93:1464-1469, 1996); removal of these two transporter molecules, or other MHC intracellular trafficking systems may also provide a means to reduce or eliminate transplantation rejection. As an alternative to a universal donor approach to histocompatibility, genetic manipulation could be used to generate "custom" MHC profiles to match individual needs.

In addition to manipulating MHC expression, for human transplantation, cells and tissues from EBD cells and cell lines of the invention can also be manipulated to eliminate or reduce other cell-surface marker molecules that induce tissue/organ graft rejection. The present invention encompasses all such modifications that reduce or eliminate allogenic (e.g., organ graft) rejection when employing cells, cell lines (or any parts or derivatives thereof) derived from the cells of the present invention.

Tissue Engineering

The invention provides human cells and methods that can be used to produce or reconstruct a tissue or organ, including in vitro or vivo regeneration, and engineering of artificial organs or organoids. In one aspect, the EBD cells of the invention are pre-cultured under conditions that promote generation of a desired differentiated, or restricted, cell lineage. The culture conditions can also be manipulated to generate a specific cell architecture, such as the three-dimensional cellular arrangements and relationships seen in specialized structures, such as neuromuscular junctions and neural synapses, or organs, such as livers, and the like.

These conditions can include the use of bioreactor systems to influence the generation of the desired cell type. Bioreactor systems are commonly used in the art of tissue engineering to create artificial tissues and organs. Some bioreactor systems are designed to provide physiological stimuli similar to those found in the natural environments. Others are designed to provide a three-dimensional architecture to develop an organ culture. For example, the compositions (including bioreactors, scaffolds, culture devices, three-dimensional cell culture systems, and the like) and methods described in U.S. Pat. Nos. 6,143,293; 6,121,042; 6,110,487; 6,103,255; 6,080,581; 6,048,721; 6,022,743; 6,022,742; 6,008,049; 6,001,642; 5,989,913; 5,962,325; 5,858,721; 5,843,766; 5,792,603; 5,770,417; 5,763,279; 5,688,687; 5,612,188; 5,571,720; 5,770,417; 5,626,863; 5,523,228; 5,459,069; 5,449,617; 5,424,209; 5,416,022; 5,266,480; 5,223,428; 5,041,138; and 5,032,508; or variations thereof, can be used in conjunction with this invention.

As discussed above, production of cells, tissues and organs for transplantation may require combinations of genetic modifications, in vitro differentiation, and defined substrate utilization of the cells of the invention to generate the desired altered cell phenotype and, if a tissue or organ is to be generated, the necessary three-dimensional architecture required for functionality. For example, a replacement organ may require vasculature to deliver nutrients, remove waste products, and deliver products, as well as specific cell-cell contacts. A diverse cell population will be required to carry out these and other specialized functions, such as the capacity to repopulate by lineage-restricted stem cells.

Further examples of the use of the EBD cells of the invention and their differentiated derivatives include generation of non-cellular structures such as bone or cartilage replacements.

These cells can be used as a source of genetic material such as nuclei, genomic DNA, chromosomes, genes, RNA, and cDNAs. These materials can be used to construct libraries and screening arrays used to discover markers, e.g., of pluripotency and of differentiation. These cells can be used as a source of unmodified or genetically modified organelles such as nuclei and mitochondria. These cells can be used to develop antibodies useful in the study of early human development. Intact wild type, genetically altered, physically or biochemically altered, or differentiated cells or their membrane extracts can be used as immunogens for the formation of mono- or polyclonal antibodies to cell surface molecules.

These cells can be used for transplantation to non-human animals; if desired, such cells may be genetically modified for purposes of gene therapy. For example, exogenous MHC or other foreign or endogenous antigens and/or genes that will decrease rejection by the host organism of these transplanted materials are produced by means of the present invention. Molecules, proteins, cells, tissues, organs, fluids, or cell products are harvested from cells, cell lines, cell cultures for xenotransplantation.

In vitro methods for enrichment, selection and genetic manipulation are used to generate a diverse set of cell types and populations from the EBD cells of the invention. As discussed above, these cells can be used in the formation of artificial tissue, organs or organoids to be used in implants and transplants, particularly human transplantations. Unstructured populations of EBD cell types can also be directly administered, e.g., to the general vascular system, independently or to complement a tissue or organ transplantation. This approach does not necessarily require that the cells are homogenous or have been specifically directed into a particular lineage or cell type. Animal models of human disorders can be used to test transplantation and implantation treatments using the EBD cells, tissue and organs of the invention. Immunosuppressive agents (e.g., cyclosporin A) can also be used (and tested in the animal models). The fate of injected cells can be followed using a transfected marker, e.g., LacA, a pulse labeling agent, e.g., brdU (1 to 10 µM) or bis-benzimide, a human specific but cell independent marker such as an antibody or a housekeeping gene, or a human specific antibody that is specific to a gene product produced by the desired differentiated cell type. Beyond tracing the expression of markers and measurements of engraftment and cell survival, functional rescue of cells and the modeled disorder can be determined.

Objective tests are used to determine the efficacy of treatment. For example, human EBD cells of the invention are injected into the dorsal spinal column of a test animal, e.g., a myelin deficient rat. Several weeks after the injection the fate (e.g., their survival, their differentiation into another cell type, e.g., a glial cell capable of myelination) of the implanted EBD cells is determined. This can be done using antibodies, e.g., to PLP, myelin basic protein (MBP), CNP, GFAP and the like; see, e.g., Brustle, 1999, supra, for an exemplary protocol. Human EBD cells of the invention can also be implanted to treat spinal cord pathologies and injuries, e.g., crush injuries, and their survival and differentiation into, e.g., neuronal and glial cells can be determined; see, e.g., McDonald, *Nat. Med.* 51:410-1412, 1999, for an exemplary protocol. Human EBD cells of the invention can also be implanted by intra-cerebroventricular injection; animal models can also be used to test the efficacy of this treatment, e.g., injection into a shiverer mouse (see, e.g., Wolf, *Dev. Neurosci.* 21:483-90, 1999).

Human EBD cells of the invention can also be implanted into the central nervous system (CNS) for the treatment of disease or physical brain injury, such as ischemia or chemical injury; animal models can also be used to test the efficacy of this treatment, e.g., injection of compounds like 60HAD, or, fluid percussion injury (see, e.g., Carbonell, *Acta Neuropathol.* (*Berl.*) 98:396-406, 1999) can serve as a model for human brain injury. In these animal models, the efficacy of administration of the EBD cells of the invention is determined by the recovery of improvement of injury related deficits, e.g., motor or behavioral deficits. See, e.g., Borlongan, *Exp. Neurol.* 149:310-321, 1998 (using human embryonal carcinoma-derived cells, NT2N), and, Svendsen, *Exp. Neurol.* 148:135-146, 1997 (using primary human fetal CNS cells), for exemplary protocols. Human EBD cells of the invention can also be implanted into the central nervous system (CNS) for the treatment of amyotropic lateral sclerosis (ALS); animal models can also be used to test the efficacy of this treatment, e.g., the SODI mutant mouse model (see, e.g., Dupuis, *Neurobiol. Dis.* 7:274-785, 2000). Human EBD cells of the invention can also be implanted into the central nervous system (CNS) for the treatment of Alzheimer's disease; one animal model that can be used to test the efficacy of this treatment is the mutant presenilin I mouse (see, e.g., Van Dorpe, *Am. J. Pathol.* 157:1283-1298, 2000). Human EBD cells of the invention can also be implanted into the central nervous system (CNS) for the treatment of Parkinson's disease, efficacy of this treatment can be assessed using, e.g., the MPTP mouse model (see, e.g., Lee, *J. Neurochem.* 75:521-531, 2000).

Human EBD cells of the invention can also be used to treat diseases of cardiac, skeletal or smooth muscles; cells can be directly injected into or near desired sites. The survival and differential of these cells can be determined by monitoring the expression of appropriate markers, e.g, human muscle-specific gene products (see, e.g., Klug, 1996, supra; Soonpaa, *Science* 264:98-101, 1994; Klug, *Am. J. Physiol.* 269:H1913-H1921, 1995; implanting fetal cardiomyocytes and mouse ES-derived cells), for exemplary protocols.

Human EBD cells of the invention can also be used to treat diseases of the liver or pancreas. Cells can be directly injected into the hepatic duct or the associated vasculature. Similarly, cells could be delivered into the pancreas by direct implantation or by injection into the vasculature. Cells engraft into the liver or pancreatic parenchyma, taking on the functions normally associated with hepatocytes or pancreatic cells, respectively. As with other implantations, cell survival, differentiation and function can be monitored by, e.g., immunohistochemical staining, or PCR, of specific gene products.

Human EBD cells of the invention can also be used to treat diseases, injuries or other conditions in or related to the eyes. Cells can be directly injected into the retina, optic nerve or other eye structure. In one aspect, cells differentiate into retinal epithelia, nerve cells or other related cell types. As with other engraftments, cell survival, differentiation and function can be monitored by, e.g., immunohistochemical staining, or PCR, of specific gene products.

Human EBD cells of the invention can also be used to treat vascular diseases or other related conditions by repopulation of the vasculature with, e.g., vascular endothelium, vascular smooth muscle and other related cell types. For example, an injured vein or artery is treated by implantation of EBD cells of the invention; these cells re-populate the appropriate injured sites in the vasculature. The cells can be implanted/ injected into the general circulation, by local ("regional") injection (e.g., into a specific organ) or by local injection, e.g., into a temporarily isolated region. In an alternative procedure, a reconstructed or a completely new vasculature can be constructed on a biomatrix or in an organotypic culture, as described herein.

Human EBD cells of the invention can also be used to repopulate bone marrow, e.g., in situations where bone marrow has been ablated, e.g., by irradiation for the treatment of certain cancers. Protocols for these treatments can be optimized using animal models, e.g., in animals whose endogenous bone marrow has been ablated. EBD cells of the invention can be injected into the circulatory system or directly into the marrow space of such an animal (e.g., a rodent model). Injection of the human cells of the invention would allow for the re-population of bone marrow, as well as engraftment of a wide range of tissues and organs. If the animals are sublethally irradiated, the efficacy of the cells can be monitored by tracking animal survival, as without bone marrow re-population the animal will die. The hematopoietic fate of the injected cells also can be examined by determining the type and amount to human cell colonies in the spleen.

In another aspect, the human EBD cells of the invention can be used in organotypic co-culture. This system offers the benefits of direct cell application and visualization found in in vitro methods with the complex and physiologically relevant milieu of an in vivo application. In one aspect, a section of tissue or an organ specimen is placed into a specialized culture environment that allows sufficient nutrient access and gas exchange to maintain cellular viability. Human EBD cells (including differentiated cell types) of the invention are then placed on, into or in the proximity of the tissue or organ piece. The human cells of the invention then migrate over or into the tissue or organ and may differentiate in ways that may not be easily replicated in a purely in vitro environment. An exemplary organotypic culture system incorporates a rat spinal cord; sections of rat spinal cord are placed on a media permeable membrane that is suspended in growth media near the media/atmosphere interface. EBD cells of the invention are placed on, into or in the proximity of the sections. After a period of time, the fate of the human cells is traced by, e.g., immunocytochemical or PCR methods to detect specific neural gene products.

In using the human EBD cells, or differentiated derivatives thereof, of the invention to construct artificial organs or organoids, bioengineered matrices or lattice structures can be populated by single or successive application of these human cells. The matrices can provide structural support and architectural cues for the repopulating cells.

EBD Cells as a Source of Stage-Specific and Developmental Antigens

In one aspect of the invention, EBD cells and cell lines are used for immunohistological studies of early human development. Antibodies (e.g., monoclonal antibodies) specific for cell surface antigens unique to specific stages of development can be generated using the cells of the invention; such antigens can include polysaccharides, glycolipids, and glycoproteins (see, e.g., U.S. Pat. No. 5,453,357). For example, antibodies that bind to cell surface glycolipids and glycoproteins have been used to study human germ cell tumors (see, e.g., Labosky, *Development* 120:3197-3204, 1994) and other cancers (see, e.g., Thomson, *Proc. Natl. Acad. Sci. USA* 92:7844-7848, 1995).

Methods of producing polyclonal and monoclonal antibodies are known to those of skill in the art and described in the scientific and patent literature, see, e.g., Coligan, CURRENT PROTOCOLS IN IMMUNOLOGY, Wiley/Greene, N.Y., 1991; Stites (eds.) BASIC AND CLINICAL IMMUNOLOGY (7th ed.) Lange Medical Publications, Los Altos, Calif. ("Stites"); Goding, MONOCLONAL ANTIBODIES PRINCIPLES AND PRACTICE (2d ed.) Academic Press, New York, N.Y., 1986; Harlow, ANTIBODIES, A LABORATORY MANUAL, Cold Spring Harbor Publications, New York, 1988.

Antibodies also can be generated in vitro, e.g., using recombinant antibody binding site expressing phage display libraries, in addition to the traditional in vivo methods using animals. See, e.g., Huse, *Science* 246:1275, 1989; Ward, *Nature* 341:544, 1989; Hoogenboom, *Trends Biotechnol.* 15:62-70, 1997; Katz, *Annu. Rev. Biophys. Biomol. Struct.* 26:27-45, 1997. Human antibodies can be generated in mice engineered to produce only human antibodies, as described by, e.g., U.S. Pat. Nos. 5,877,397; 5,874,299; 5,789,650; and 5,939,598. B-cells from these mice can be immortalized using standard techniques (e.g., by fusing with an immortalizing cell line such as a myeloma or by manipulating such B-cells by other techniques to perpetuate a cell line) to produce a monoclonal human antibody-producing cell. See, e.g., U.S. Pat. Nos. 5,916,771; 5,985,615.

EBD Cells as Sources of Macromolecules

The EBD cells and cell lines of the invention can also be used in the biosynthetic production of macromolecules. Non-limiting examples of products that could be produced are blood proteins, hormones, growth factors, cytokines, enzymes, receptors, binding proteins, signal transduction molecules, cell surface antigens, and structural molecules. Factors produced by undifferentiated, differentiating, or differentiated EBD cells would closely simulate the subtle folding and secondary processing of native human factors produced in vivo. Biosynthetic production by EBD cells and cell lines can also involve genetic manipulation followed by in vitro growth and/or differentiation. Biosynthetic products can be secreted into the growth media or produced intracellularly or contained within the cell membrane, and harvested after cell disruption. Genetic modification of the gene coding for the macromolecule to be biosynthetically produced can be used to alter its characteristics in order to supplement or enhance functionality. In this way, novel enhanced-property macromolecules can be created and pharmaceuticals, diagnostics, or antibodies, used in manufacturing or processing, can be produced. Pharmaceutical, therapeutic, processing, manufacturing or compositional proteins that may be produced in this manner include, e.g., blood proteins (clotting factors VIII and IX, complement factors or components, hemoglobins or other blood proteins and the like); hormones (insulin, growth hormone, thyroid hormone, gonadotrophins, PMSG trophic hormones, prolactin, oxytocin, dopamine, catecholamines and the like); growth factors (EGF, PDGF, NGF, IGF and the like); cytokines (interleukins, CSF, GMCSF, TNF, TGFα, TGFβ, and the like); enzymes (tissue plasminogen activator, streptokinase, cholesterol biosynthetic or degradative, digestive, steroidogenic, kinases, phosphodiesterases, methylases, de-methylases, dehydrogenases, cellulases, proteases, lipases, phospholipases, aromatase, cytochromes adenylate or guanylate cyclases and the like); hormone or other receptors (LDL, HDL, steroid, protein, peptide, lipid or prostaglandin and the like); binding proteins (steroid binding proteins, growth hormone or growth factor binding proteins and the like); immune system proteins (antibodies, SLA or MHC gene products); antigens (bacterial, parasitic, viral, allergens, and the like); translation or transcription factors, oncoproteins or proto-oncoproteins, milk proteins (caseins, lactalbumins, whey and the like); muscle proteins (myosin, tropomyosin, and the like).

In another use of the invention, EG cells or their differentiating or differentiated derivatives can be used in the construction and testing of human artificial chromosomes.

EXAMPLES

The following examples are intended to illustrate but not limit the invention. While they are typical of those that might be used, other procedures known to those skilled in the art may alternatively be used.

Example 1

Collection of Human Primordial Germ Cells and Derivation of Embryonic Germ (EG) Cells The following example demonstrates exemplary methods for the production and culture of human embryonic germ (EG) cells from human primordial germ cells (PGC).

Gonadal anlagen or genital ridges with mesenteries were dissected from 8-11 week LMP (last menstrual period) human aborted fetal material. The genital ridges were rinsed with 0.5 ml phosphate buffered saline solution or other isotonic buffer (PBS 0.21 g/L $KH_2PO_4$; 9 g/L NaCL; 0.726 g/L $Na_2HPO_4/7H_2O$), then placed into 0.1 ml 0.5% trypsin-0.53 mM sodium EDTA solution (BRL) and was cut into small (less than 1 $mm^3$) chunks. The chunks were then further minced with a fine forceps. The tissue was then repeatedly pipetted through a 100 ul pipet tip to further disaggregate the cells. The tissue and cell suspension was incubated at 37° C. for approximately 5 min., then approximately 3.5 ml EG growth media (defined as D-MEM, 4500 mg/L D-glucose, 2200 mg/L mM sodium bicarbonate; 15% ES qualified fetal calf serum (BRL); 2 mM glutamine (BRL); 1 mM Sodium Pyruvate (BRL); 1000-2000 U/ml human recombinant leukemia inhibitory factor (LIF, Genzyme); 1 to 2 ng/ml human recombinant basic fibroblast growth factor (bFGF, Genzyme); and 10 µM Forskolin in 10% DMSO) was added.

Approximately 0.2 ml of the cell suspension was added to each of 16 wells of a 96-well tissue culture plate previously prepared with a sub confluent layer of STO mouse fibroblasts that had been cultured for 3 days in a modified EG growth media that did not contain LIF, bFGF or Forskolin, then irradiated with 5000 rad of gamma irradiation.

The human PGC cells and STO mouse fibroblasts were cultured for a first passage 7-10 days in EG growth media at 37° C. with 5% CO2 at 90% humidity. Growth media was freshly prepared and replaced daily. Alternatively, subconfluent fibroblast cells can be irradiated, then plated into tissue culture plates to form a feeder layer. The PGC cells were trypsinized and each well was passaged to 1 well of a 24-well culture dish previously prepared with irradiated STO mouse fibroblasts (90% of the cells) and to 1 well of a 96-well tissue culture plate previously prepared with irradiated STO mouse fibroblasts (90% of the cells). The cells were cultured with daily replacement of growth media until cells morphology consistent with murine EG cells were observed, typically, 7-30 days with 1 to 4 passages. Depending on the age of the tissue from which the PGCs were obtained, this process could take one or more passages. On the 13th day of culture (three days after subculture), a subset of cells growing on the 96-well culture dish were fixed and stained for the presence of alkaline phosphatase by using a commercially available diagnostic kit (Sigma Chemicals, product number 86-R). The cells were washed 2 times with phosphate buffered saline (PBS) then fixed for 30 seconds in a mixture of 25 ml citrate solution (18 mM sodium citrate, 9 mM sodium chloride, pH 3.6), 65 ml acetone and 8 ml of 37% formaldehyde. Fixed cells were then incubated in the dark for 15 min. in alkaline-dye mixture. The cells are then rinsed with deionized water for 2 min. and allowed to dry. Alkaline phosphatase positive PGC and EG cells stain red, while cells that lack alkaline phosphatase activity, such as STO cells, remain clear. Cells growing on the 24-well plate were passaged four times to expand cell numbers, and multiple frozen stocks from each passage were prepared. Cells were photographed throughout the initial 13 days of culture using phase contrast microscopy and selected cells were processed for alkaline phosphatase staining as described herein.

In an alternate approach, EG cells were isolated using hyaluronidase/collagenase/DNase. Gonadal anlagen or genital ridges with mesenteries were dissected from 8-11 week LMP human aborted fetal material. The genital ridges were rinsed in PBS then placed in 0.1 ml HCD digestion solution (0.01% hyaluronidase type V, 0.002% DNase I, 0.1% collagenase type IV (all from Sigma) prepared in EG growth media). Tissues were cut and minced with a fine forceps in a small glass (preferred) or plastic dish then transferred by pipet to a microfuge tube and incubated 1 hour to overnight 37° C. Approximately 1 ml of EG growth media was then added, and the tissue and cell suspension was centrifuged at 500 rpm for 5 min. The tissue and cells were then resuspended in 1 to 3 ml of EG growth media, and plated into a recipient dish containing a feeder layer as described above.

For subsequent passages, cells were rinsed in PBS then HCD digestion solution was added. Digestion times ranged from 20 min. to 2 hours, and were monitored microscopically to determine completion. Cells were pumped several times with a pipet, then approximately 10 volumes of EG growth media were added. The tissue and cells were then removed to a tube and centrifuged at 500 rpm for 5 min. The tissue and cells were then resuspended in EG growth media, and plated into a recipient dish containing a feeder layer as described above.

Example 2

Culturing and Characterization of EG Cells and Formation of Embryoid Bodies

The following example demonstrates exemplary methods for the production, culture and characterization of EG cell cultures derived from human PGCs, and their aggregation into human embryoid bodies (EBs), and the characterization of EBD cells.

Gonadal ridge and mesenteries of 5 to 9 week post-fertilization human embryos were dissociated with 0.25% trypsin-EDTA and mechanical disruption. Tissues were initially cultured, and subsequently passaged, on an irradiated mouse STO fibroblast feeder layer in DMEM supplemented with 15% FBS, human recombinant leukemia inhibitory factor (hrLIF), human recombinant basic fibroblast growth factor (hrbFGF) and forskolin. For alkaline phosphatase activity detection, cells were fixed in 66% acetone/3% formaldehyde then stained with naphthyl/FRV alkaline AP substrate (Sigma). For immunocytochemistry, cells were fixed in 3% buffered paraformaldehyde. Antibody detection was done using biotinylated anti-mouse antibodies, strepavidin conjugated horseradish peroxidase, and AEC chromagen (Bio-Genex, San Ramon, Calif.). Cells prepared for cytogenetic analysis were treated with 0.1 ug/ml Colecimd, 0.075M KCl, then 3:1 methanol acetic acid fix.

To establish human EG cell lines, gonadal ridge and mesenteries of 5-9 week post-fertilization embryos (obtained as the result of pregnancy termination) were cultured on mouse STO fibroblast feeder layers in the presence of a variety of growth factors, including human recombinant leukemia inhibitory factor (hrLIF), human recombinant basic fibroblast growth factor (hrbFGF), and forskolin. Initially, single PGCs were visualized by alkaline phosphatase (AP) staining. Over a period of 7-21 days, these PGCs gave rise to large multicellular colonies resembling those of early passage mouse EG and ES cell colonies. Throughout the culture period and with subsequent passages, the cells continued to be AP positive. The cells were also positive when tested against a panel of five monoclonal antibodies (SSEA-1, SSEA-3, SSEA-4, TRA-1-60 [ATCC HB-4783], TRA-1-81 [ATCC HB-4784]) used routinely to characterize pluripotent stem cells. The cultured cells have been continuously passaged and found to be karyotypically normal and stable. Both XX and XY cell cultures have been obtained. The properties so far characterized on the derived human cells are consistent with those anticipated for pluripotent stem cells, as summarized in TABLE 1.

TABLE 1

| Antibody Name | Antigen | Antigen type | hPGC-derived | hEC | mES | EC | ES | EG |
|---|---|---|---|---|---|---|---|---|
| MC480 | SSEA-1 | glycolipid (lacto) | + | − | − | + | + | + |
| MC631 | SSEA-3 | glycolipid (globo) | +/− | + | + | − | − | − |
| MC813-70 | SSEA-4 | glycolipid (globo) | + | + | + | − | +/− | + |
| TRA-1-60 | | glycoprotein | + | + | + | − | − | − |
| TRA-1-81 | | glycoprotein | + | + | + | − | − | − |

Antibody reactivity to primate and mouse cell lines. Abbreviations are as follows: hPGC, human primordial germ cell; hEC, human embryonal carcinoma; mES, monkey embryonic stem cell; EG, embryonic germ cell.

Several human PGC-derived cell cultures were obtained. All cultures tested shared the morphological, immunological, and karyotypic characteristics described. During standard culture, a small fraction of colonies spontaneously differentiated into EB structures (i.e., embryoid bodies (EBs). When analyzed by electron microscopy, a wide variety of cell types were identified, including an epithelial outer layer covering a partially solid core of fibroblasts, endothelial cells, and what appear to be anucleated red blood cells.

Example 3

Generation of Human Embryoid Bodies (EBs) and Harvesting of EBD Cells

The following example demonstrates exemplary methods for the production and culture of human embryoid bodies (EBs) and the characterization and use of EBD cells.

To EBs are physically removed from the stem cell culture medium where they are formed, and placed in a calcium and magnesium-free phosphate-buffered saline (PBS). The EBs are then sorted into categories by gross morphology, e.g., cystic or solid. After sorting, the EBs are transferred to a mixture of one mg/ml collagenase and dispase enzyme (Boehringer Mannheim), and incubated for 30 minutes to three hours at 37° C.; during this time they are manually agitated or triturated every about 10 to 30 minutes. Other dissociation treatments can be used, e.g., the individual or combined use of several different types of collagenase, dispase I, dispase II, hyaluronidase, papain, proteinase K, neuraminidase and/or trypsin. Each treatment requires optimization of incubation length and effectiveness; cell viability can be monitored visually or by trypan blue exclusion followed by microscopic examination of a small aliquot of the disaggregation reaction. One collagenase/dispase disaggregation protocol calls for incubation for about 30 minutes at 37° C.; this results in between about 10% and 95% of the EB constituent cells disaggregated into single cells. Large clumps of cell may remain intact.

After disaggregation, one to five mls of growth media are added to the cells. One exemplary media comprises RPMI base media with about 10 to 20% fetal calf serum supplemented with antibiotics, e.g., penicillin and streptomycin. The cell suspension is then centrifuged at about 100 to 500 g for about five minutes. The supernatant is then removed and replaced with fresh growth media. The cells are resuspended and plated into a tissue culture vessel that can be coated with cells or a biomatrix.

The choice of growth media, vessel and biomatrix substrate is variable and depends on the number of cells disaggregated and the type of differentiated and lineage-restricted cells that are desired. The specific conditions can be made general in order to allow the proliferation of a wide variety of cells, or, the conditions can be tailored to select or enhance for specific cell types, or, if it is desired to grow/engineer tissues and organs. The result may be pure and uniform populations of cells, or, a mixture of cells. A therapeutic use may require an enriched but mixed population of cells of different phenotypes or stages of development. A therapeutic use may require a mixed population of cells that can take on a variety of differentiated tasks or may benefit from the application of highly enriched or pure clonal populations.

For example, EBD cells obtained from 4 to 8 EBs can be resuspended in media, e.g., about three ml media (e.g., RPMI), and plated (e.g., into a 3.5 cm diameter plate) onto a surface that has been coated with a collagen (e.g., rat tail collagen I; that can be prepared and used as described by manufacturer (e.g., Collaborative Biomedical Products). The culture media is replaced every two to three days. This is a non-specific method that will allow a wide variety of cell types to proliferate.

Additional methods employ specialized media and growth substrates to enhance, select or direct the growth of particular cell types. For example, the culture media can comprise reduced serum; or, it can be serum-free, in order to fully define and control the growth processes and avoid the uncontrolled effects of serum components. These uncontrolled effects can be due to the presence of a wide and variable variety of growth factors known to be present in serum. Some examples of serum-free media or reduced serum media are EGM2mv (Clonetics), various muscle-specific growth media and hepatocyte maintenance media (Hepatostim, Collaborative BioAlliance, Stony Brook, N.Y.). Some additional examples of adhesion matrices are human extracellular matrix extract (hECM) and Matrigel™ (Collaborative Biomedical Products), laminin, poly(L)-ornithine and fibronectin. Growth media can be further enhanced with a wide variety of compounds including, but not limited to, retinoic acid, dimethylsulfoxide (DMSO), cAMP elevators such as forskolin, isobutylmethylxanthine, and dibutryl cAMP, cytokines such as basic fibroblast growth factor, epidermal growth factor, platelet derived growth factor (PDGF and PDGF-AA) nerve growth factor, T3, sonic hedgehog (Shh or N-Terminal fragment), ciliary neurotrophic factor (CNTF), erythropoeitin (EPO) and bone morphogenic factors.

Human embryonic germ (EG) cells derived from primordial germ cells (PGCs) were isolated and cultured as described in Example 1, above; see also U.S. Pat. No. 6,090,622). EBs, seen as differentiated cell structures, were formed in the presence of 1000 U/ml human recombinant leukemia inhibitory factor (LIF, Genzyme Corp., Cambridge, Mass.); 1 ng/ml human recombinant basic fibroblast growth factor (bFGF, Genzyme); and 10 μM Forskolin in 15% fetal calf serum (Hyclone).

Cystic EBs were removed from culture by using a forceps and were disaggregated by digestion in 1 mg/ml collagenase/dispase (Roche) for about 30 minutes to one hour at 37° C. EBs from four distinct genotypes were prepared, designated LV, SL, LU2 and QE.

Cells were then spun at 1000 rpm, about five minutes and resuspended in various growth media and matrix environments. The approach was taken in order to identify environments that promoted vigorous proliferation of a wide variety of cell types known to be present in the EBs (see Example 1, above). Of growth environments tested, EGM2mv (Clonetics, BioWhittaker, Walkersville, Md.) media and a plating surface of collagen I produced the greatest cell proliferation. For this reason this combination was used in subsequent cloning and transfection experiments.

RPMI growth media comprised RPMI 1640™ (LTI), 15% FCS, non-essential amino acids, 100 U/ml penicillin, 100 μg/ml streptomycin, EGM2mv media (which contains 5% FCS), hydrocortisone, hbFGF, hVEGF, $R^3$-IGF-1, ascorbic acid, HEGF, heparin, gentamycin, amphotericin. Hepatostim media (Becton Dickinson), which is a modified Williams E medium supplemented with 10 ng/ml hEGF, 1 μM dexamethasone, 6.25 μg/ml insulin, 6.25 μg/ml transferrin, 6.25 ng/ml selenious acid, 1.25 mg/ml BSA, 5.35 μg/ml linoleic acid, 2 mM L-glutamate. ITSFn media (see, e.g., Brustle, *Science* 285:754, 1999), which is DMEM/F12 supplemented with 5 μg/ml insulin, 50 μg/ml transferrin, 30 mM selenium chloride, 5 μg/ml fibronectin. Matrices included bovine collagen I (Collaborative Bioscience) at 10 μg/cm$^2$, and human extracellular matrix (Collaborative Bioscience) at 5 μg/cm$^2$. Cells were cultured at 37° C., 5% CO$_2$, 95% humidity and routinely passaged at 1:10 to 1:40 by using 0.05% trypsin, 0.53 EDTA (LTI), for 5 min., 37° C. Low serum and serum free media cultures were treated with trypsin inhibitor (Clonetics) and spun down and resuspended in growth media. Cells were cryopreserved in the presence of 40% FCS, 10% DMSO in a controlled rate freezing vessel, and stored in liquid nitrogen. The cultures LV, SL, LU2 were derived from EG cell cultures initiated from 7, 8 and 9 week LMP gonadal ridge tissue.

Cells prepared for cytogenetic analysis were incubated in growth media with 0.1 μg/ml of Colcemid for about 3 to 4 hours, trypsinized, resuspended in 0.075 M KCl, and incubated for 20 min. at 37° C., then fixed in 3:1 methanol/acetic acid.

Clonal lines were generated by low-density plating followed by cloning cylinder isolation. Stable transfection of human EBD cultures was carried out by lipofection. One to five μg/ml of a construct containing the neomycin phosphotransferase gene flanked by the mouse phosphoglycerate kinase-1 (PGK-1) was used to transfect about 2×10$^5$ cells; lipofectamine plus lipid (LTI) was used according to manufacturers instructions. Stably transfected cells were selected by growth in media supplemented with 200 μg/ml G418 and isolated using cloning cylinders.

Several different media/matrix combinations were used to provide selective advantage to certain cell types and thereby differentially enrich the EB outgrowth cultures. A reverse transcriptase PCR (RT-PCR) expression profile was performed (see below for protocol details) on twenty-four genes in order to classify the resultant cell populations from three genetically distinct cell cultures LS, LV and LU2. Table 1 summarizes various differentiation markers found in the EBD cells. Markers were chosen to indicate expression profiles of four cell lineages; neural, muscle, vascular and endoderm (see the PCR primer pairs listed in Table 3, below).

mRNAs corresponding to the neural progenitor markers nestin (NEST), vimentin (VIM), astrocyte marker GFAP, the visceral endoderm marker AFP (AFP), and the vascular/hematopoietic marker Flk1 (VEGF receptor) (Flk1) were detected by PCR; this indicated that these mRNAs were expressed under all eight media/matrix combinations. No expression of the muscle markers myoD and myogenin (myog) or the endoderm/liver markers aldolase B (ALDB), liver pyruvate kinase (LPK), albumin (ALB), HNF3β or HNF4α was detected in any of the cell cultures.

Individual growth environments produced different gene expression patterns. The EGM2MV/collagen I environment that produced the highest rate of cell proliferation resulted in a culture containing cells that also express CD34. Expression of the other markers varied with culture conditions and genotype. For instance, in the LV culture, the endoderm marker GATA4 was expressed only when grown in the EGM2MV/collagen I environment, while in the SL culture, all environments results in GATA4 expression. AC 133 (a cell surface marker of hematopoietic stem cells) had weak or absent expression in all conditions except RPMI/collagen and to a lesser extent RPMI/hECM in the SL culture.

Expression of markers from several different lineages, as they have been commonly defined, can be due to multiple cell types within the culture or can result from a multi- or pluripotent cell capable of many distinct patterns of expression and physiological roles. In order to resolve this issue in these human cell cultures, 13 clonal lines were isolated from the LV culture and a PCR expression profile (as above) was carried out on each. Nestin and vimentin expression was retained in all the LV clonal lines, while expression of the other markers varied substantially.

Although the mixed culture expression should be the sum representative of the individual clones, cell changes during clone isolation and enrichment for certain mRNAs may allow for clonal lines that express mRNA not detected in the mixed culture. For example, the muscle marker myf6 is detected in LV-13, -14 and -32 lines. The mRNA for AFP was not or only weakly detected in LV-17 and -27. Clearly, multiple cell subtypes exist within the mixed cultures. However, within each of the clonal lines mRNA expression of markers for a wide variety of lineages was detected. The possibility of culture expression drift was examined by comparison of the mRNA expression of a low passage EGM2MV culture and one that had undergone greater than 200 population doublings in sixteen passages. Little difference was observed except for the apparent accentuation of some markers in the later passage cells.

For the reverse transcriptase PCR (RT-PCR) expression profile, RNA was prepared from cells growing on 60-mm tissue culture plates by using the Qiagen miniprep kit. RNA preparations were digested with RNase-free DNase (Roche), 30 min. at 37° C. and then the digest was inactivated at 75° C. for 5 min. Synthesis of cDNA was performed on 5 μg RNA by using oligo (dT) primers and a standard MMLV (LTI) reaction carried out at 42° C. Thirty cycles of polymerase chain reaction (PCR) were carried out in the presence of 1.5 mM $MgCl_2$ with an annealing temperature of 55° C. and incubation times of 30 sec. PCR reactions were resolved on a 1.8% agarose gel. The efficacy of all PCRs was established by using appropriate commercially available human tissue RNA (Clonetech). Some gels were subject to Southern blot analysis by using oligonucleotide probes end-labeled with $^{32}P$-ATP, hybridized in 6×SSC, 5×Denhardt's Solution, 0.1% SDS, 0.05% sodium pyrophosphate, 100 μg/ml sheared and denatured salmon sperm DNA at 45° C. cDNA synthesis and genomic DNA contamination were monitored by primers specific to human phosphoglycerate kinase-1 (PGK-1), which give products of approximately 250 base pairs (bp) and approximately 500 bp when amplifying cDNA and genomic DNA, respectively. Ethidium bromide fluorescence of agarose gel resolved PCR amplimers and immunocytochemical reactivities were subjectively assigned to 1 of 4 intensity categories; very strong, strong, detected, and not detected.

In order to corroborate the reverse transcriptase PCR results and to further define the capacity of human EBD cells to express markers of widely differing developmental lineages, immuno-cytochemical and surface marker binding assays were performed on several cell cultures. Based on the strong and consistent mRNA expression of neural markers in the three mixed cultures under different growth environments, and 13 clonal lines, it was decided to further investigate the expression profiles of these cells using a variety of neuronal and glial specific antibodies. In addition, the expression of endodermal marker AFP, and markers of vascular endothelium (flk1, acetylated low density lipoprotein binding, AcLDL) was investigated.

For immunocytochemistry activity assays, approximately $1 \times 10^5$ cells were plated in each well of an 8-well glass bottom chamber slide. Cells were fixed in either a 4% paraformaldehyde in phosphate buffered saline (PBS) or a 1:1 mixture of methanol/acetone for 10 min. as recommended by the antibody manufacturer. Cells were permeabilized in 0.1% Triton X-100, 1×PBS for 10 min. if required, then blocked in either Powerblock™ (BioGenex, San Ramon, Calif.), 5% fetal bovine serum, or 1 to 5% goat serum supplemented with 0.5% bovine serum albumin for 10-60 min. as recommended by the antibody manufacturer. Primary antibodies and dilutions were as follows: neurofilament 68 kDa (Roche, 1:4), neuron specific enolase (Pharmingen, 1:100), β tubulin (Pharmingen, one to 5 μg/ml), tau (Pharmingen, 5 μg/ml), vimentin (Roche, 1:10), nestin (NIH, 1:250), glial fibrillary associated protein (GFAP) Pharmingen, one to ten μg/ml), VEGF receptor (Flk1) (Santa Cruz Biotech, 1:2000). Detection was carried out by secondary antibodies conjugated to biotin, strepavidin-conjugated horseradish peroxidase, 3-amino-9-ethylcarbazole chromagen (BioGenex). Acetylated low-density lipoprotein linked to the fluorescent dye DiI (AcLDL-DiI, Molecular Probes) was added directly to the culture medium at a final concentration of 5 μg/ml with culture medium and was incubated 4 hours at 37° C. Cells were then washed by incubation in media without AcLDL-DiI for 15 min. at 37° C., then 3 times with 1×PBS. The cells were then fixed in 10% PBS buffered formalin for 10 min., then covered with a small volume of PBS and cover-slipped. Cells were then visualized by using a fluorescent microscope.

The immunocytochemistry data agreed with the PCR experimental results: all cell cultures were strongly reactive for nestin, vimentin, β tubulin and GFAP. Additionally, the cells grown in the three original environments were reactive with the Flk1 antibody; however, cells from cultures plated in the fully defined environments were not. Only cells grown in RPMI containing environments were reactive with antibodies to neuron specific enolase. In this case, the cells grown on hECM were slightly more reactive than those grown on collagen I, and both were weak in comparison to the other antibodies. No culture conditions produced cells that were reactive to antibodies specific for the neurofilament 68K chain or tau. If the cultures were at all reactive for an antibody, they were uniformly so, with virtually no cells failing to stain. As predicted by PCR, these cells were simultaneously expressing markers of distinctly different lineages.

Within a mixed population of cells resulting from EBs being disaggregated in one mg/ml collagenase/dispase and grown in RPMI media supplemented with 15% fetal calf serum on a collagen I matrix, individual cells that were positive for vascular endothelial markers Flk1 and AcLDL-DiI were identified. Individual cells within the cultures also stained positive for the endodermal marker AFP.

The influence of Matrigel™ (Collaborative Biosciences) on EBD cell cultures was determined. Cells were plated into Matrigel™ at 150 to 300 µl/cm$^2$ and grown up to several months by replacing the media weekly. Disaggregation was carried out by digestion in dispase (Collaborative Biosciences) for two hours at 37° C. For immuno-histochemical analysis of cells growing in Matrigel™ extracellular matrix, cells were fixed in 10% PBS buffered formalin/0.1% Triton X-100 for ten min. prior to antibody staining for confocal analysis or 10% PBS buffered formalin for 10 min. then embedded in 3% agarose and fixed overnight.

Often cells in Matrigel™ shift from a proliferative form to a more differentiated and non-proliferative one. In order to investigate whether the EBD cells of the invention were capable of proliferating in Matrigel™, several EBs or "nests" were collected and disaggregated by digestion in dispase. Disaggregated single cells that were re-plated into a thick layer of Matrigel™ slowly formed the highly branched and extended morphology seen in cells of the original "nests." However, in one month, these single cells did not form independent complex structures or seem to have proliferated. If the Matrigel™ disaggregated cells were plated onto thin layers of collagen I, glass or plastic, they reverted to an adherent cell morphology and did not proliferate extensively.

Genetic modification of the mixed cell culture can be used to further influence the type of cells that are obtained in this process. This can be achieved by insertion (e.g., transfection or infection) of a selectable marker construct or by expression of a particular transcription factor. Delivery of this construct can be by any means, e.g., it can be lipid-based or by calcium phosphate or electroporation or viral methods.

In order to demonstrate the capacity of human EBD cells to take up and stably integrate recombinant DNA, a lipid-based transfection experiment was undertaken. A DNA construct consisting of a constitutive promoter to mouse phosphoglucokinase was linked to the gene conferring resistance to neomycin phosphotransferase. This construct was then introduced into human EBD cells of the invention using Lipofectin-Plus™ (LTI) by using manufacturer's supplied protocol. The efficiency of stable integration was approximately one in $1 \times 10^5$ cells grown in EGM2MV media and plated in collagen I. Two neomycin resistant EBD clonal lines were obtained. The methods of the invention also comprise optimization of these transfection including lipofection, protocols. Retroviral and viral vectors are also used to genetically manipulate the EG cells, or EBD cells of the invention (see Example 4). Alternative protocols or nucleic acid insertion modalities can routinely modified and incorporated to optimize results for the desired result for a particular cell type.

Another exemplary genetic selection construct used in the methods of the invention incorporates a tissue-specific gene promoter that drives the transcription of an antibiotic resistance gene. Only the desired cell types, defined by their utilization of a specific gene promoter, would survive the antibiotic treatment (e.g., neomycin or hygromycin). For example, a highly pure population of cardiomyocytes from differentiated EBD cells can be produced by genetic selection using, e.g., a tissue-specific promoter, such as the alpha-cardiac myocin heavy chain promoter, joined to a cDNA coding for an antibiotic (e.g., neomycin) resistance; using this method (Klug, *J. Clin. Invest.* 98:216-224, 1996), produced cardiomyocytes from differentiated mouse ES cells.

Transcription factor expression is another exemplary method for the controlled differentiation of EBD cells of the invention. As developmental commitment decisions are usually hierarchical, it is desirable to choose a transcription factor that is active in early stages of development. The promoter driving the expression can be a strong constitutive promoter, a tissue-specific promoter, or an inducible promoter; or, an exogenously regulated promoter such as the commercially available tetracycline (Clontech) and ecodysone (Invitrogen, San Diego, Calif.) expression systems. EBD cells of the invention can be so manipulated to generate skeletal muscle cells by constitutive expression of MyoD1; using this method, Dekel (*New Biol.* 4:217-224, 1992) and Shani (*Symp. Soc. Exp. Biol.* 4619-36, 1992) generated skeletal muscle cells from mouse ES cells. EBD cells of the invention can be so manipulated to generate neurons by constitutive expression of neuroD2 or neuroD3; using this method, O'Shea (*Soc. Neurosci. Abstr.* 23:1144, 1997) generated neurons from mouse ES cells.

This genetic approach is also used to enhance and control the proliferation of EBD cells of the invention (and, as for all methods described herein, the cell lines and differentiated progeny of these cells). Control of proliferation is particularly useful on EBD differentiated cells because in many instances differentiated cell types have a limited proliferative capacity. Exemplary approaches include the delivery of genes known to influence cell proliferation, such as the wild type Simian virus 40 (SV40) large T antigen, a temperature sensitive SV40 large T antigen, a telomerase, such as the human telomerase reverse transcriptase (TERT, see above). Expression of these genes can be controlled to allow for proliferation only when desired.

As discussed above, genetic manipulation can also be used to modify the immune recognition of these cells. Such cells can be used individually or to generate engineered tissues and organs for transplantation/implantation (see above).

Non-genetic approaches can also be used to enrich and select for desired cell types. Fluorescent activated cell sorting (FACS) can be used to selectively enrich for or to remove cell types based on recognition of cell surface antigens. Differential dye absorption can also be used. One exemplary method enriches for human vascular endothelium by sorting EBD mixed cell populations for the presence of CD34 and/or Flk1 antigens. Differential dye absorption can be carried out on bone marrow and muscle-derived stem cells as described by Bussoni, *Nature* 401:390-394, 1999. Hematopoietic cells can also be enriched using these in vitro enrichment and selection techniques. As discussed above, by using cytokines (and different matrices, media, etc.), the EBD cells of the invention can be directed to generate a variety of blood cell types; methods analogous to those used by Keller, *Blood* 88:863-869, 1996; Keller, *Curr. Opin. Cell Biol.* 7:862-869, 1995; Keller, *Mol. Cell Biol.* 13:473-486, 1993; Wiles, *Development* 111:259-267, 1991, who differentiated mouse ES cells into most or all of the blood cells, can be used. These cells can be identified morphologically or by their expression of specific gene products by, e.g., PCR or immunocytochemistry.

Example 4

Production of EBD Cell Cultures

The following example demonstrates exemplary methods for the production and culture of novel human embryoid bodies (EBs) of the invention and the characterization and use of EBD cells. The isolation and culture of cells from human EBs as well as characterization of their gene expression during growth in several different culture environments is described. The EBD cells of the invention develop as heterogeneous cell cultures capable of robust and long-term (>70 PD, population doublings) proliferation in culture. They have normal karyotypes, can be cryopreserved, clonally isolated and stably transfected. Cell cultures and clonal lines of EBD cells of the invention retain a broad pattern of gene expression, including, significantly, simultaneous expression of markers normally associated with cells of neural, vascular/hematopoietic, muscle and endoderm lineages. Clonally isolated EBD cell lines of the invention simultaneously express a wide array of mRNA and protein markers that are normally associated with distinct developmental lineages.

The growth and expression characteristics of these EBD cells demonstrate that they are relatively uncommitted precursor or progenitor cells. EBD cells of the invention also are useful for studies of human cell differentiation and for transplantation therapies.

Human pluripotent stem cell cultures were derived from primordial germ cells, isolated and cultured as described above and in Shamblott et al., *Proc. Natl. Acad. Sci. USA* 95:13726-13731, 1998). Four genetically distinct human EG cell cultures were selected to represent the range of developmental stages at which human EG cultures can be initiated, with karyotypes as noted LV (46, XX), SL (46, XY), LU2 (46, XY) and SD (46, XX). These cultures were derived and cultured from 5, 6, 7, and 11 week post-fertilization primordial germ cells (PGCs), respectively. EBs were formed in the presence of leukemia inhibitory factor (LIF, 1000 U/ml), basic fibroblast growth factor (bFGF, 2 ng/ml), forskolin (10 µM) and 15% fetal calf serum (FCS, Hyclone). During routine growth, 1 to 5% of the multicellular EG colonies formed large fluid-filled cystic EBs that were loosely attached to a remaining EG colony or to the fibroblast feeder layer. Approximately 10 cystic EBs from each culture were dissociated by digestion 1 mg/ml in Collagenase/Dispase (Roche Molecular Biochemicals) for 30 min. to 1 hour at 37° C. Cells were then spun at 1000 rpm for 5 min.

EB constituent cells were then resuspended and replated in three (LV) or six (SL, LU2 or SD) growth media and biomatrix combinations in an effort to identify environments that promoted vigorous cell proliferation with the possibility of differential enrichment of outgrowth populations. Two growth medias were selected in order to investigate the effects of serum and specific mitogens on the proliferation of these human cells. RPMI 1640 (LTI) (15% FCS, 0.1 mM nonessential amino acids, 2 nM L-glutamine, 100 U/ml penicillin, 100 µg/ml streptomycin) supplemented with 15% fetal calf serum is a simple base media that relies on serum to support cell proliferation. EGM2MV media (Clonetics, San Diego) (5% FCS, hydrocortisone, human basic fibroblast growth factor, human vascular epidermal growth factor, R(3)-insulin-like growth factor-I, ascorbic acid, human epidermal growth factor, heparin, gentamycin, and amphotericin) has a reduced serum content (5%) with added growth factors. Three cell attachment surfaces were used: bovine collagen I (Collaborative Biomedical, 10 µg/cm$^2$), human extracellular matrix (Collaborative Biomedical, 5 µg/cm$^2$), and tissue culture plastic. Cells were cultured at 37° C., 5% $CO_2$, 95% humidity and routinely passaged 1:10 to 1:40 by using 0.025% trypsin, 0.01% EDTA (Clonetics) for 5 min. at 37° C. Low serum cultures were treated with trypsin inhibitor (Clonetics) and then spun down and resuspended in growth media. Cell were cryopreserved in the presence of 50% FCS, 10% dimethylsulfoxide (DMSO) in a controlled rate freezing vessel, and stored in liquid nitrogen.

All six growth environments supported cell proliferation and the resultant cells were designated EBD (EBD) cell cultures.

Cell proliferation studies carried out on several genetically distinct EBD cultures by plating 1×10$^4$ cells of EBD culture SD into 35 mm dishes containing the growth environment in which they were derived. Cells from three wells were grown until subconfluent, and then trypsinized, diluted 1:10, replated, grown and counted. Student's t-tests (n=3) were performed to assign significance. Clonal lines were generated from EBD culture LV by low-density plating in EGM2MV media on Collagen I ("LVEC") followed by cloning cylinder isolation and expansion to >1×10$^6$ cells. Cloning efficiency was determined by low density plating of a total of 600 LVEC cells. Methylene Blue staining to identify colonies was performed 10 days after plating. "PD" levels were calculated as 3.32 (log cells$_{harvested}$–log cells$_{plated}$) and do not include cell division during the initial phase of culture derivation. These cell proliferation studies indicated that EGM2MV medium was superior to RPMI 1640 medium (P<0.001) and that extracellular matrix and collagen I were superior to tissue culture plastic (P<0.001).

Karyotypic analysis performed on each culture at approximately 20 PD indicated that the cells had a normal diploid chromosomal complement. Cells prepared for cytogenetic analysis were incubated in growth media with 0.1 µg/ml of colcemid/2.5 µg/ml ethidium bromide for 3 hours, trypsinized, resuspended in 0.075 M KCl, incubated for 35 min. at 37° C., and then fixed in 3:1 methanol/acetic acid.

Example 5

Gene Transfer into EBD Cell Cultures

The ability of EBD cells to be stably transfected in the EGM2MV/collagen I environment was examined by stable lipofection of human EBD cells (from cell cultures) with neomycin resistance gene driven by the mouse phosphoglucokinase I promoter. Briefly, 1 to 5 µg of a construct containing the neomycin phosphotransferase gene flanked by the mouse phosphogycerate kinase-1 (PGK-1) was used to transfect approximately 2×10$^5$ cells by using Lipofectamine plus lipid (LTI). Stably transfected cells were selected by growth on collagen I in EGM2MV media supplemented with 200 to 400 µg/ml G418 and isolated by using cloning cylinders. Stable integration efficiencies of approximately 1×10$^{-5}$ were routinely obtained, and neomycin resistant clonal lines could be expanded to >1×10$^6$ cells.

In an effort to improve integration efficiency, retroviral and lentiviral transduction were investigated. Retroviral transduction of culture LVEC was carried out by using the MGIN vector (SyStemix, Inc., Palo Alto, Calif.) and amphotropic viral envelope as reported (Cheng et al., *Gene Ther.* 4:1013-1022, 1997). This vector uses the retroviral long terminal repeat (LTR) to drive transcription of enhanced green fluorescence protein (EGFP) and neomycin phosphotransferase coding regions. Lentiviral transduction was carried out by using the EF.GFP vector (see, e.g., Akagi, *Kidney Int.* 51:1265-1269, 1997) in which the human elongation factor 1α promoter drives the transcription of EGFP in an HIV-1-based self-inactivating lentiviral backbone. EF.GFP virus was produced by co-transfection of 293T cells with a packaging plasmid expressing HIV-1 gag/pol, REV and TAT proteins, and a plasmid expressing the VSV-G envelope. Viral titers were determined by the number of GFP expressing 293T cells after infection. For the EBD cell transduction, $1 \times 10^5$ LVEC cells were infected with $1 \times 10^6$ transducing units of either retrovirus or lentivirus in the presence of 8 μg/ml polybrene overnight for two successive days. Transduced cells were analyzed for GFP expression by using fluorescence-activated cell sorting (FACS) analysis six days after plating and proliferation in the absence of drug selection. Mock-infected cells were used to establish the level of background fluorescence. Retrovirally transduced LVEC cells were selected by growth in the presence of 400 μg/ml G418. When cultures of LVEC were infected with equal titers of either retrovirus or lentivirus carrying enhanced green fluorescent protein (EGFP) expression vectors, the efficiencies were approximately 30% and 98%, respectively, and remained constant for greater than two weeks. The retrovirally transduced LVEC culture was essentially 100% EGFP positive after two weeks of drug selection and remained so for greater than 30 PD.

Example 6

Immunochemistry

In an effort to classify these EBD cells by their expression characteristics, the presence of neural progenitor, neuronal and glial markers was determined. Neural progenitors are capable of generating both neurons and glia, and are known to express the intermediate filament proteins nestin and vimentin. Additionally, several neuronal and glial markers were used in this survey, including the neuronal markers neurofilament light isoform (NFL), tau, neurofilament heavy isoform (SMI32), and neuron specific enolase (NSE); and the glial markers 2', 3'-cyclic nucleotide 3' phosphodiesterase (CNPase), galactocerebroside (GALC), and O4 (oligodendroglial) antigen. For immunocytochemistry activity assays, approximately $1 \times 10^5$ cells were plated in each well of an 8-well glass bottom chamber slide. Cells were fixed in either 4% paraformaldehyde in phosphate buffered saline (PBS) or a 1:1 mixture of methanol/acetone for 10 min. as recommended by the antibody manufacturer. Cells were permeabilized in 0.1% Triton X-100, 1×PBS for 10 min. if required, then blocked in either Powerblock™ (BioGenex, San Ramon, Calif.), 5% fetal bovine serum, or 1 to 5% goat serum supplemented with 0.5% bovine serum albumin for 10-60 min. as recommended by the antibody manufacturer. Primary antibodies and dilutions were as follows: neurofilament 68 kDA (Roche, 1:4), neuron-specific enolase (PharMingen, 1:100), tau (Pharmingen, 5 μg/ml), vimentin (Roche, 1:10), human nestin (NIH, 1:250), galactocerebroside (Sigma, 1:500); 2', 3'-cyclic nucleotide 3'-phosphodiesterase (Sigma, 1:500), O4 (Roche, 10 μg/ml), SMI32 (Stemberger monoclonal, 1:5000). Antibodies reactive to the astrocyte marker glial fibrillary acidic protein (GFAP) and neuronal marker β tubulin type III were not included, as conditions for their specific reactivity could not be established. Detection was carried out by secondary antibodies conjugated to biotin, strepavidin-conjugated horseradish peroxidase, and 3-amino-9-ethylcarbazole chromagen (BioGenex).

Cells of the EBD culture LVEC were strongly immunoreactive to the nestin- and vimentin-specific antibodies (greater than 95% cells positive). Cells were less strongly and/or less consistently immunoreactive (10% to 50% cells positive) to antibodies specific for NFL, tau, NSE, SMI32, CNPase and GALC. No cells immunoreactive for the O4 antigen were detected.

Example 7 mRNA Expression Profiles

To confirm some of the antibody staining results and to expand the range of markers examined, a 24-gene reverse transcriptase PCT (RT-PCR) expression profile was carried out on the LVEC culture and other EBD cultures. Markers were chosen to indicate expression profiles of four cell lineages known to be present in human EBs: neural, muscle, vascular/hematopoietic and endoderm (Shamblott et al., *Proc. Natl. Acad. Sci. USA* 95:13726-13731, 1998). Vascular and hematopoietic cell lineages were grouped because they share the markers that were employed. Additionally, the nine antibodies described above were used to confirm the expression status results of the four PCR reactions and to extend the analysis to antigens not readily amenable to PCR. Expression of markers not verified by antibody staining was confirmed by Southern blot hybridization of PCR products to specific internal oligonucleotide probes. When possible, several markers of a lineage or cell type were used. The neural lineage markers were the most strongly and consistently expressed.

RNA was prepared from cells growing on 60-mm tissue culture plates by using the Qiagen miniprep kit. RNA preparations were digested with RNAse-free DNAse (Roche) 30 min. at 37° C. and then the digest was inactivated at 75° C. for 5 min. Synthesis of cDNA was performed on 5 μg RNA by using oligo (dT) primers and a standard MMLV (LTI) reaction carried out at 42° C. Thirty cycles of polymerase chain reaction (PCR) were carried out in the presence of 1.5 mM $MgCl_2$ with an annealing temperature of 55° C. and incubation times of 30 sec. PCR reactions were resolved on a 1.8% agarose gel. The efficacy of all PCRs were established by using appropriate commercially available human tissue RNA (Clonetech). Some gels were subjected to Southern blot analysis by using oligonucleotide probes end-labeled with $^{32}$P-ATP, hybridized in 6×SSC, 5×Denhardt's Solution, 0.1% SDS, 0.05%: sodium phophosphate, 100 μg/ml sheared and denatured salmon sperm DNA at 45° C. cDNA synthesis and genomic DNA contamination were monitored by primers specific to human phosphoglycerate kinase-1 (PGK-I), which give products of approximately 250 bp and approximately 500 bp when amplifying cDNA and genomic DNA, respectively. Ethidium bromide fluorescence of agarose gel resolved PCR amplimers and immunocytochemical reactivities were subjectively assigned to 1 of 4 intensity categories; very strong, strong, detected, and not detected. PCR primer and probe sequences appear in Table 2 below.

TABLE 2

| Lineage | Marker name | Primer/probe | Size (bp) | Sequence (5'-3') | |
|---|---|---|---|---|---|
| Neural | Nestin | Nestin-N<br>Nestin-C<br>Nestin-P | 200 | GCCCTGACCACTCCAGTTTA<br>GGAGTCCTGGATTTCCTTCC<br>TAAGGATGGAGAATCCGGTG | SEQ ID NO: 1<br>SEQ ID NO: 2<br>SEQ ID NO: 3 |
| | MAP2 | MAP2-N<br>MAP2-C<br>MAP2-P | 200 | GCATATGCGCTGATTCTTCA<br>CTTTCCGTTCATCTGCCATT<br>AACCGAGGAAGCATTGATTG | SEQ ID NO: 4<br>SEQ ID NO: 5<br>SEQ ID NO: 6 |
| | Neurofilament light | NFL-N<br>NFL-C<br>NFL-P | 200 | ACCCGACTCAGTTTCACCAG<br>TCAGCCTTAGACGCCTCAAT<br>CTATCTGATGTCCACCCGCT | SEQ ID NO: 7<br>SEQ ID NO: 8<br>SEQ ID NO: 9 |
| | Vimentin | Vimentin-N<br>Vimentin-C<br>Vimentin-P | 200 | GGGACCTCTACGAGGAGGAG<br>CGCATTGTCAACATCCTGTC<br>CGAAAACACCCTGCAATCTT | SEQ ID NO: 10<br>SEQ ID NO: 11<br>SEQ ID NO: 12 |
| | Tyrosine hydroxylase | TYRH-N<br>TYRH-C<br>TYRH-P | 188 | GTGTTCCAGTGCACCCAGTA<br>AGCGTGGACAGCTTCTCAAT<br>CAGTTCTCGCAGGACATTGG | SEQ ID NO: 13<br>SEQ ID NO: 14<br>SEQ ID NO: 15 |
| | Sox-1 | SOX1-N<br>SOX1-C<br>SOX1-P | 199 | AGAACCCCAAGATGCACAAC<br>GCCAGCGAGTACTTGTCCTT<br>AGTGGAGGTCATGTCCGAG | SEQ ID NO: 16<br>SEQ ID NO: 17<br>SEQ ID NO: 18 |
| | Sox-2 | SOX2-N<br>SOX2-C<br>SOX2-P | 200 | AGAACCCCAAGATGCACAAC<br>GGGCAGCGTGTACTTATCCT<br>GTTCATCGACGAGGCTAAGC | SEQ ID NO: 19<br>SEQ ID NO: 20<br>SEQ ID NO: 21 |
| | GFAP | GFAP-N<br>GFAP-C<br>GFAP-P | 199 | ACCAGGACCTGCTCAATGTC<br>ATCTCCACGGTCTTCACCAC<br>ACATCGAGATCGCCACCTAC | SEQ ID NO: 22<br>SEQ ID NO: 23<br>SEQ ID NO: 24 |
| Muscle | myf5 | myf5-N<br>myf5-C<br>myf5-P | 193 | TCACCTCCTCAGAGCAACCT<br>TGAAGCCTTCTTCGTCCTGT<br>TTCTTCCAGGAGGGCCTAAT | SEQ ID NO: 25<br>SEQ ID NO: 26<br>SEQ ID NO: 27 |
| | Myogenin | Myogenin-N<br>Myogenin-C<br>Myogenin-P | 199 | GCCAGACTATCCCCTTCCTC<br>GAGGCCGCGTTATGATAAAA<br>CCTTTCCAGGGAGGTAAAGC | SEQ ID NO: 28<br>SEQ ID NO: 29<br>SEQ ID NO: 30 |
| | MyoD | myoD-N<br>myoD-C<br>myoD-P | 196 | GTGAGACCCTCGCAGACCTA<br>CTCCTCTCTGGCAAACGAAC<br>CACTCCGGTCCCAAATGTAG | SEQ ID NO: 31<br>SEQ ID NO: 32<br>SEQ ID NO: 33 |
| | myf6 | myf6-N<br>myf6-C<br>myf6-P | 200 | TTCGATGCCTTTCTTCCATC<br>ACTTTTCGGTCTGGGTTCCT<br>GTGGAGGAAGTGGTGGAGAA | SEQ ID NO: 34<br>SEQ ID NO: 35<br>SEQ ID NO: 36 |
| | Myosin heavy chain α | MHC-N<br>MHC-C<br>MHC-P | 199 | GGAGGAGGACAGGAAAAACC<br>CAGCTTGTTGACCTGGGACT<br>GGACCTGGTAGACAAGCTGC | SEQ ID NO: 37<br>SEQ ID NO: 38<br>SEQ ID NO. 39 |
| | Myosin light 2V | MLC-N<br>MLC-C<br>MLC-P | 200 | GGCGAGTGAACGTGAAAAAT<br>CAGCATTTCCCGAACGTAAT<br>CCCTGAGGAAACCATTCTCA | SEQ ID NO: 40<br>SEQ ID NO: 41<br>SEQ ID NO: 42 |
| Vascular | CD34 | CD34-N<br>CD34-C<br>CD34-P | 200 | TGAAGCCTAGCCTGTCACCT<br>CGCACAGCTGGAGGTCTTAT<br>CTAGCCTTGCAACATCTCCC | SEQ ID NO: 43<br>SEQ ID NO: 44<br>SEQ ID NO: 45 |
| | flk-1 | flk1-N<br>flk1-C<br>flk1-P | 199 | GGTATTGGCAGTTGGAGGAA<br>ACATTTGCCGCTTGGATAAC<br>GCCAAGCTGTCTCAGTGACA | SEQ ID NO: 46<br>SEQ ID NO: 47<br>SEQ ID NO: 48 |
| | Ac133 | AC133-N<br>AC133-C<br>AC133-P | 200 | CAGTCTGACCAGCGTGAAAA<br>GGCCATCCAAATCTGTCCTA<br>CTGCGGTCATCTCTCAATGA | SEQ ID NO: 49<br>SEQ ID NO: 50<br>SEQ ID NO: 51 |
| Endoderm | α-1-fetoprotein | AFP-for<br>AFP-rev<br>AFP-P | 200 | AGCTTGGTGGTGGATGAAAC<br>TCCAACAGGCCTGAGAAATC<br>CTTGTGAAGCAAAAGCCACA | SEQ ID NO: 52<br>SEQ ID NO: 53<br>SEQ ID NO: 54 |
| | Albumin | ALB-N<br>ALB-C<br>ALB-P | 233 | CCACGACAACGAAGAAACCT<br>CAGAAGACGCCTTACCTTCG<br>TACCTGTACGAAATCGCACG | SEQ ID NO: 55<br>SEQ ID NO: 56<br>SEQ ID NO: 57 |

TABLE 2-continued

| Lineage | Marker name | Primer/probe | Size (bp) | Sequence (5'-3') | |
|---------|-------------|--------------|-----------|------------------|---|
| | HNF3 β | HNF3B-N | 199 | CTACGCCAACATGAACTCCA | SEQ ID NO: 58 |
| | | HNF3B-C | | GAGGTCCATGATCCACTGGT | SEQ ID NO: 59 |
| | | HNF3B-P | | GCCCTACTCGTACATCTCGC | SEQ ID NO: 60 |
| | HNF4 α | HNF4A-N | 501 | TCTCATGTTGAAGCCACTGC | SEQ ID NO: 61 |
| | | HNF4A-C | | GGTTTGTTTTCTCGGGTTGA | SEQ ID NO: 62 |
| | | HNF4A-P | | GCAGGGTCTAGAAGGCTGTG | SEQ ID NO: 63 |
| | GATA4 | GATA4-N | 194 | TCCCTCTTCCCTCCTCAAAT | SEQ ID NO: 64 |
| | | GATA4-C | | TCAGCGTGTAAAGGCATCTG | SEQ ID NO: 65 |
| | | GATA4-P | | CGACAATCTGGTTAGGGGAA | SEQ ID NO: 66 |
| | Aldolase B | ALDB-N | 195 | TGGCATCTGCTTTTTGTCTG | SEQ ID NO: 67 |
| | | ALDB-C | | CGCTTCATAAAAGCCTCCTG | SEQ ID NO: 68 |
| | | ALDB-P | | CAACCTTTGCCCTCTACCAA | SEQ ID NO: 69 |
| | Liver pyruvate kinase | LPK-N | 496 | GCTTCGGTCATGGGTCTCTA | SEQ ID NO: 70 |
| | | LPK-C | | CTCCACTTCCGACTCTGGAC | SEQ ID NO: 71 |
| | | LPK-P | | GTGGAGAGCTTTGCAGGTTC | SEQ ID NO: 72 |
| Control | PGK-1 | PGK-N | 250 | CAGTTTGGAGCTCCTGGAAG | SEQ ID NO: 73 |
| | | PGK-C | | TGCAAATCCAGGGTGCAGTG | SEQ ID NO: 74 |

Results are shown in FIG. 1. Neural progenitor markers nestin and vimentin, and astrocyte marker glial fibrillary acidic protein (GFAP) were expressed in all cell cultures. The neuronal markers NFL, microtubule-associated protein 2C (MAP2C), tau, non-phosphorylated neurofilament heavy isoform (SMI32), neuronal-specific enolase (NSE) and tyrosine hydroxylase (TYRH) were weakly expressed in many of the cultures, with occasionally stronger expression of tau and SM132 when cultures SL and LU2 were grown in EGM2MV media on human extracellular matrix or on tissue culture plastic. CNPase and GALC are specifically expressed in oligodendrocytes and Schwann cells (Springle et al., *Brain Res.* 426:349-357, 1987; Raff et al., *Nature (London)* 274:813-816, 1978). Both markers were strongly expressed in most of the EBD cultures. No expression of SOX1, SOX2 or O4 was detected.

In general, the muscle markers were most weakly and sporadically expressed. Expression of the muscle-specific developmental genes myf5, myogenin and myoD or myosin heavy chain alpha was not detected. However, expression of myf6 was detected in cultures SL and LV, and expression of myosin light-chain 2 ventricular isoform was detected in some cultures.

The vascular/hematopoietic stem cell marker CD34 was expressed most strongly by culture LVEC but was detectable in culture LU2. Flk1 (VEGF receptor-2) was expressed by all four cultures, with strongest expression by cells growing in EGM2MV media. AC 133 (CD133) is a cell-surface marker of vascular/hematopoietic stem and progenitor cells (Yin et al., *Blood* 90:5002-5012, 1997; Miraglia et al., *Blood* 91:4390-4391, 1998) that is also expressed in some human epithelial cells (Corbeil et al., *J. Biol. Chem.* 275:5512-5520, 2000). Expression of AC133 in EBD cell cultures was restricted to SL and LU2, with the strongest expression in SL growing in RPMI media on collagen I (SLRC).

The endoderm marker alpha-1-fetoprotein (AFP) was expressed in all instances. GATA4, which is expressed in endoderm and heart (Arceci et al., *Mol. Cell. Biol.* 13:2235-2246, 1993), was also expressed in most of the cultures. Hepatic nuclear factor 3β (HNF3β) is expressed in many endodermal derivatives such as liver (Ang et al., *Development (Cambridge, U.K.)* 119:1301-1315, 1993) and is an essential early factor in pancreatic development (Wu et al., *Mol. Cell. Biol.* 17:6002-6013, 1997). HNF3P expression was only detected when EGM2MV media was used, and then only in two cultures. Hepatic nuclear factor 4α (HNF4α) expression is regulated by HNF 3β (Duncan et al., *Science* 281:692-695, 1998) and was only detected in one instance, coincident with the strongest expression of HNF 3β. No expression of the liver-specific markers aldolase B, liver pyruvate kinase, or albumin was detected in any of the cultures.

Figure 2:
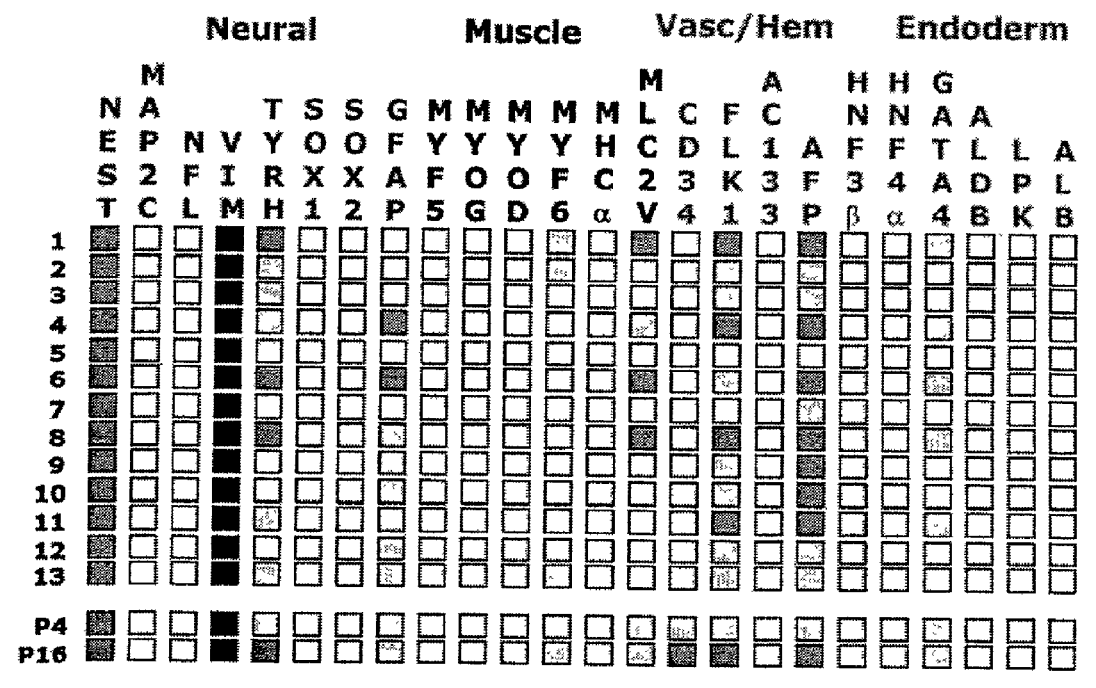

Simultaneous expression of markers from several different lineages, as they have been commonly defined, can be due to multiple cell types within the culture or result from cells capable of multilineage expression. To resolve this issue in the mixed EBD cell cultures, mRNA expression profiles were carried out on 13 clonal lines isolated from the LVEC culture. Results are shown in FIG. 2. Nestin and vimentin expression was retained in all of the LVEC clonal lines, consistent with the uniform immunocytochemical staining of the LVEC culture for these markers. Expression of the other markers varied substantially. In 11 of 13 lines, mRNA expression of markers from all four lineages was detected. Although the mixed culture expression should be the sum representative of the individual clones, variation during clone isolation and enrichment for certain mRNAs allow for clonal lines that express mRNA not detected in the mixed culture. For example, the muscle marker myf6 is detected in LV-1, -2, and -13 but not in the low passage LVEC mixed culture. In general, the cloning efficiency of LVEC cells was approximately 29% (173 colonies/600 cells plated). In the isolation of these LV clones, 69% (27 of 39) of the isolated colonies were capable of expansion to greater than $10^6$ cells.

The possibilities of culture expression drift and variability due to assay artifacts was further examined by comparison of the mRNA expression of low-passage LVEC culture and one that had undergone approximately 70 PD in 16 passages. Little difference was observed in the marker expression levels except for the apparent accentuation of some markers, including myf6, in the later passage cells. In this case, when signal levels were normalized against the expression of nestin or a phosphoglycerate kinase-1 control, no obvious differences were apparent. The change in expression levels of markers not expressed in the LVEC culture were not determined; however, decreased immunoreactivity to AC133 has been noted following continuous passage of culture SLRC.

The growth environments that we have studied had a significant effect on the proliferation of EBD cells but did not predictably influence their gene expression profiles. This was not unexpected, as EBs are heterogeneous with respect to cell type content and the environments were designed to be generally supportive rather than specifically tailored to a particular cell type. This was substantiated by differences in EBD expression profiles when multiple cultures were initiated in parallel or serially from one EG culture. The strongest and most consistent antibody and PCR markers were markers associated with neural lineages. A neural identity of cells derived from hPSCs is not surprising, as neural cells can be routinely obtained from mouse ES, EG, and embryonal carcinoma cultures as well as human embryonal carcinoma cultures (Andrews, *Dev. Biol.* 103:285-293, 1984). However, EBD cell cultures and clonal lines cannot be viewed simply as neuronal progenitors, as they simultaneously express markers from multiple, distinct cell lineages. Multilineage gene expression has been reported in other precursor or progenitor cell populations but not with such a broad range. Neuronal progenitors simultaneously express neuronal and glial markers (Colucci-D'Amato et al., *Exp. Cell Res.* 252:383-391, 1999; Piper et al., *J. Neurophysiol.* 84:534-548, 2000), and multipotent hematopoietic progenitors simultaneously express a variety of lineage-affiliated transcription factors and cytokine receptors (Hu et al., *Genes Dev.* 11:774-785, 1997). The breadth of expression exhibited by EBD cultures and clonal lines may be unique to these cells or an outcome of the experimental culture design. The multilineage expression exhibited by EBD cells may represent the basis for the developmental plasticity observed after the differentiation of bone marrow (Petersen et al., *Science* 284:1168-1170, 1999) and central nervous system stem cells (Bjornson et al., *Science* 283:534-537, 1999). In this model, multilineage gene expression by precursor or progenitor cells defines a ground state from which cell-extrinsic and cell-intrinsic signals work to continuously define a differentiated expression pattern and phenotype (Enver et al., *Blood* 92:348-352, 1998).

Example 8

Telomerase Activity Assays

To determine the proliferative capacity of EBD cultures, LVEC, SLEC, LU2EC and SDEC were continuously passaged. After approximately 70-80 PD, these cultures failed to divide. Continuous passage of cultures in environments less favorable to proliferation has not been carried out; however, most EBD cultures are capable of at least 40 PD. To determine whether the proliferation of EBD cultures may be limited by the absence of telomerase, telomeric repeat amplification protocol assays were performed on LVEC and SDEC cultures that had undergone approximately 20 PD after EBD cell establishment. Telomerase assays were performed by using a telomeric repeat amplification protocol followed by ELISA detection of amplified products (TeloTAGGG PCR ELISA PLUS™, Roche). No telomerase activity was detected in either culture, consistent with the hypothesis that cell division in the absence of telomerase activity leads to cellular senescence.

Example 9

Tumor Formation

The ability of EBD cells to proliferate in vivo was examined by injection of LVEC cells into immunocompromised mice. Three female 6-week old SCID-NOD mice were injected with $3 \times 10^6$ EBD cells (LVEC) or $2.5 \times 10^5$ to $1 \times 10^6$ mouse ES cells (ES D3) in the left and right calf muscle, respectively. After 1 month, animals were killed and visually examined for tumors. Injected calf muscles were dissected intact, fixed in 4% phosphate buffered paraformaldehyde overnight, then processed and imbedded in paraffin. Sections stained with hematoxylin and eosin were examined. No tumors were detected two months post-injection, whereas large teratocarcinomas formed when an equal number of, or as little as $2.5 \times 10^5$, mouse ES cells were injected similarly.

Example 10

Analysis of Media Components Needed for Culture of EBD Cells

In order to establish a defined serum-free media for EBD cell proliferation and differentiation, we investigated the effects of Knockout™ serum replacement media (Gibco/BRL) and the components of EGM2mv media (Clonetics) on the proliferation of EBD culture LVEC. Briefly, $1 \times 10^4$ EBD cells were plated on a 10 cm tissue culture dish coated with collagen I and containing one of several experimental media. The cells were then dissociated by standard trypsinization and counted using a hemocytometer. Three counts were made from each cell population and a mean and standard deviation were determined.

The first experimental group was designed to determine the optimal concentration of Knockout serum in EGM2mv media when the normal 5% serum was omitted. E (EGM2mv with 5% serum) provided the greatest amount of cell growth. When Knockout serum replacement was used instead of serum (0, 1, 5, 10, 15, 20, 25, and 50% Knockout serum replacement), the most effective dose was determined to be between 10% and 25%. 15% was chosen for all subsequent experiments.

In addition, the effects of the non-protein components of EGM2mv on cell division were examined. Using an identical cell procedure as was described above; EKO15 (EGM2mv without serum supplemented with 15% Knockout serum replacement) was compared to media in which hydrocortisone, ascorbic acid, or both were omitted. Each protein growth factor (bFGF, EGF, IGF-1 and VEGF) was removed individually and combinatorially. From this analysis, it was concluded that bFGF (FGF-2) was the single most important mitogen, and that IGF can be omitted with little consequence to cell division rate.

A number of embodiments of the present invention have been described. Nevertheless, it will be understood that various modifications may be made without departing from the spirit and scope of the invention. Accordingly, other embodiments are within the scope of the following claims.

What is claimed is:

1. A method of obtaining a human embryoid body derived (EBD) cell comprising:
    (a) culturing primordial germ cells in a media comprising human basic fibroblast growth factor and lacking leukemia inhibitory factor under conditions that allow formation of a solid or cystic embryoid body having a 3-dimensional morphology;
    (b) disaggregating the solid or cystic embryoid body under enzymatic conditions to provide a constituent cell or embryoid body derived (EBD) cell; and
    (c) culturing the EBD cell on a defined extracellular matrix, wherein the EBD cell forms disaggregated single cells upon dissociation from embryoid bodies (EB) and proliferates for at least 30 population doublings without being immortal under the conditions of step (a).

2. The method of claim 1 comprising selecting a single EBD cell from the EBD cells and culturing the single EBD cell to produce a clonal population of cells.

3. The method of claim 1 comprising culturing the EBD cell in a media selected from the group consisting of RPMI 1640 supplemented with 15% serum and media consisting essentially of hEGF, hydrocortisone, gentamicin, amphotericin-B, fetal bovine serum, VEGF, heparin, recombinant human IGF-1 and ascorbic acid.

4. The method of claim 3 comprising culturing the EBD cell in a media consisting essentially of hEGF, hydrocortisone, gentamicin, amphotericin-B, fetal bovine serum, VEGF, heparin, recombinant human IGF-1 and ascorbic acid.

5. The method of claim 1, wherein the matrix comprises one or more defined extracellular matrix components.

6. The method of claim 5, wherein the one or more defined extracellular matrix components are selected from the group consisting of collagen I and human extracellular matrix extract.

7. The method of claim 6, wherein the one or more defined extracellular matrix components are selected from the group consisting of collagen I and human extracellular matrix extract.

8. The method of claim 1 comprising culturing the EBD cells for at least 30 population doublings.

9. The method of obtaining a human EBD cell of claim 1, wherein the enzymatic conditions include collagenase, dispase, or both.

10. The method of claim 1, further comprising expanding the EBD cells on one or more defined extracellular matrix components.

11. The method of claim 10, wherein the one or more defined extracellular matrix components are selected from the group consisting of collagen I and human extracellular matrix extract.

* * * * *

SEQUENCE LISTING

<160> NUMBER OF SEQ ID NOS: 74

<210> SEQ ID NO 1
<211> LENGTH: 20
<212> TYPE: DNA
<213> ORGANISM: Homo sapiens

<400> SEQUENCE: 1
gccctgacca ctccagttta                                               20

<210> SEQ ID NO 2
<211> LENGTH: 20
<212> TYPE: DNA
<213> ORGANISM: Homo sapiens

<400> SEQUENCE: 2
ggagtcctgg atttccttcc                                               20

<210> SEQ ID NO 3
<211> LENGTH: 20
<212> TYPE: DNA
<213> ORGANISM: Homo sapiens

<400> SEQUENCE: 3
taaggatgga gaatccggtg                                               20

<210> SEQ ID NO 4
<211> LENGTH: 20
<212> TYPE: DNA
<213> ORGANISM: Homo sapiens

<400> SEQUENCE: 4
gcatatgcgc tgattcttca                                               20

<210> SEQ ID NO 5
<211> LENGTH: 20
<212> TYPE: DNA
<213> ORGANISM: Homo sapiens

<400> SEQUENCE: 5
ctttccgttc atctgccatt                                               20

<210> SEQ ID NO 6
<211> LENGTH: 20
<212> TYPE: DNA
<213> ORGANISM: Homo sapiens

<400> SEQUENCE: 6
aaccgaggaa gcattgattg                                               20

<210> SEQ ID NO 7
<211> LENGTH: 20
<212> TYPE: DNA
<213> ORGANISM: Homo sapiens

<400> SEQUENCE: 7
acccgactca gtttcaccag                                               20

<210> SEQ ID NO 8
<211> LENGTH: 20
<212> TYPE: DNA
<213> ORGANISM: Homo sapiens

-continued

<400> SEQUENCE: 8
tcagccttag acgcctcaat                                                    20

<210> SEQ ID NO 9
<211> LENGTH: 20
<212> TYPE: DNA
<213> ORGANISM: Homo sapiens

<400> SEQUENCE: 9
ctatctgatg tccacccgct                                                    20

<210> SEQ ID NO 10
<211> LENGTH: 20
<212> TYPE: DNA
<213> ORGANISM: Homo sapiens

<400> SEQUENCE: 10
gggacctcta cgaggaggag                                                    20

<210> SEQ ID NO 11
<211> LENGTH: 20
<212> TYPE: DNA
<213> ORGANISM: Homo sapiens

<400> SEQUENCE: 11
cgcattgtca acatcctgtc                                                    20

<210> SEQ ID NO 12
<211> LENGTH: 20
<212> TYPE: DNA
<213> ORGANISM: Homo sapiens

<400> SEQUENCE: 12
cgaaaacacc ctgcaatctt                                                    20

<210> SEQ ID NO 13
<211> LENGTH: 20
<212> TYPE: DNA
<213> ORGANISM: Homo sapiens

<400> SEQUENCE: 13
gtgttccagt gcacccagta                                                    20

<210> SEQ ID NO 14
<211> LENGTH: 20
<212> TYPE: DNA
<213> ORGANISM: Homo sapiens

<400> SEQUENCE: 14
agcgtggaca gcttctcaat                                                    20

<210> SEQ ID NO 15
<211> LENGTH: 20
<212> TYPE: DNA
<213> ORGANISM: Homo sapiens

<400> SEQUENCE: 15
cagttctcgc aggacattgg                                                    20

<210> SEQ ID NO 16
<211> LENGTH: 20
<212> TYPE: DNA

<213> ORGANISM: Homo sapiens

<400> SEQUENCE: 16
agaaccccaa gatgcacaac                                               20

<210> SEQ ID NO 17
<211> LENGTH: 20
<212> TYPE: DNA
<213> ORGANISM: Homo sapiens

<400> SEQUENCE: 17
gccagcgagt acttgtcctt                                               20

<210> SEQ ID NO 18
<211> LENGTH: 20
<212> TYPE: DNA
<213> ORGANISM: Homo sapiens

<400> SEQUENCE: 18
agtggaaggt catgtccgag                                               20

<210> SEQ ID NO 19
<211> LENGTH: 20
<212> TYPE: DNA
<213> ORGANISM: Homo sapiens

<400> SEQUENCE: 19
agaaccccaa gatgcacaac                                               20

<210> SEQ ID NO 20
<211> LENGTH: 20
<212> TYPE: DNA
<213> ORGANISM: Homo sapiens

<400> SEQUENCE: 20
gggcagcgtg tacttatcct                                               20

<210> SEQ ID NO 21
<211> LENGTH: 20
<212> TYPE: DNA
<213> ORGANISM: Homo sapiens

<400> SEQUENCE: 21
gttcatcgac gaggctaagc                                               20

<210> SEQ ID NO 22
<211> LENGTH: 20
<212> TYPE: DNA
<213> ORGANISM: Homo sapiens

<400> SEQUENCE: 22
accaggacct gctcaatgtc                                               20

<210> SEQ ID NO 23
<211> LENGTH: 20
<212> TYPE: DNA
<213> ORGANISM: Homo sapiens

<400> SEQUENCE: 23
atctccacgg tcttcaccac                                               20

<210> SEQ ID NO 24
<211> LENGTH: 20

```
<212> TYPE: DNA
<213> ORGANISM: Homo sapiens

<400> SEQUENCE: 24
acatcgagat cgccacctac                                               20

<210> SEQ ID NO 25
<211> LENGTH: 20
<212> TYPE: DNA
<213> ORGANISM: Homo sapiens

<400> SEQUENCE: 25
tcacctcctc agagcaacct                                               20

<210> SEQ ID NO 26
<211> LENGTH: 20
<212> TYPE: DNA
<213> ORGANISM: Homo sapiens

<400> SEQUENCE: 26
tgaagccttc ttcgtcctgt                                               20

<210> SEQ ID NO 27
<211> LENGTH: 20
<212> TYPE: DNA
<213> ORGANISM: Homo sapiens

<400> SEQUENCE: 27
ttcttccagg agggcctaat                                               20

<210> SEQ ID NO 28
<211> LENGTH: 20
<212> TYPE: DNA
<213> ORGANISM: Homo sapiens

<400> SEQUENCE: 28
gccagactat ccccttcctc                                               20

<210> SEQ ID NO 29
<211> LENGTH: 20
<212> TYPE: DNA
<213> ORGANISM: Homo sapiens

<400> SEQUENCE: 29
gaggccgcgt tatgataaaa                                               20

<210> SEQ ID NO 30
<211> LENGTH: 20
<212> TYPE: DNA
<213> ORGANISM: Homo sapiens

<400> SEQUENCE: 30
cctttccagg gaggtaaagc                                               20

<210> SEQ ID NO 31
<211> LENGTH: 20
<212> TYPE: DNA
<213> ORGANISM: Homo sapiens

<400> SEQUENCE: 31
gtgagaccct cgcagaccta                                               20

<210> SEQ ID NO 32
```

```
<211> LENGTH: 20
<212> TYPE: DNA
<213> ORGANISM: Homo sapiens

<400> SEQUENCE: 32
ctcctctctg gcaaacgaac                                                    20

<210> SEQ ID NO 33
<211> LENGTH: 20
<212> TYPE: DNA
<213> ORGANISM: Homo sapiens

<400> SEQUENCE: 33
cactccggtc ccaaatgtag                                                    20

<210> SEQ ID NO 34
<211> LENGTH: 20
<212> TYPE: DNA
<213> ORGANISM: Homo sapiens

<400> SEQUENCE: 34
ttcgatgcct ttcttccatc                                                    20

<210> SEQ ID NO 35
<211> LENGTH: 20
<212> TYPE: DNA
<213> ORGANISM: Homo sapiens

<400> SEQUENCE: 35
acttttcggt ctgggttcct                                                    20

<210> SEQ ID NO 36
<211> LENGTH: 20
<212> TYPE: DNA
<213> ORGANISM: Homo sapiens

<400> SEQUENCE: 36
gtggaggaag tggtggagaa                                                    20

<210> SEQ ID NO 37
<211> LENGTH: 20
<212> TYPE: DNA
<213> ORGANISM: Homo sapiens

<400> SEQUENCE: 37
ggaggaggac aggaaaaacc                                                    20

<210> SEQ ID NO 38
<211> LENGTH: 20
<212> TYPE: DNA
<213> ORGANISM: Homo sapiens

<400> SEQUENCE: 38
cagcttgttg acctgggact                                                    20

<210> SEQ ID NO 39
<211> LENGTH: 20
<212> TYPE: DNA
<213> ORGANISM: Homo sapiens

<400> SEQUENCE: 39
ggacctggta gacaagctgc                                                    20
```

```
<210> SEQ ID NO 40
<211> LENGTH: 20
<212> TYPE: DNA
<213> ORGANISM: Homo sapiens

<400> SEQUENCE: 40
ggcgagtgaa cgtgaaaaat                                           20

<210> SEQ ID NO 41
<211> LENGTH: 20
<212> TYPE: DNA
<213> ORGANISM: Homo sapiens

<400> SEQUENCE: 41
cagcatttcc cgaacgtaat                                           20

<210> SEQ ID NO 42
<211> LENGTH: 20
<212> TYPE: DNA
<213> ORGANISM: Homo sapiens

<400> SEQUENCE: 42
ccctgaggaa accattctca                                           20

<210> SEQ ID NO 43
<211> LENGTH: 20
<212> TYPE: DNA
<213> ORGANISM: Homo sapiens

<400> SEQUENCE: 43
tgaagcctag cctgtcacct                                           20

<210> SEQ ID NO 44
<211> LENGTH: 20
<212> TYPE: DNA
<213> ORGANISM: Homo sapiens

<400> SEQUENCE: 44
cgcacagctg gaggtcttat                                           20

<210> SEQ ID NO 45
<211> LENGTH: 20
<212> TYPE: DNA
<213> ORGANISM: Homo sapiens

<400> SEQUENCE: 45
ctagccttgc aacatctccc                                           20

<210> SEQ ID NO 46
<211> LENGTH: 20
<212> TYPE: DNA
<213> ORGANISM: Homo sapiens

<400> SEQUENCE: 46
ggtattggca gttggaggaa                                           20

<210> SEQ ID NO 47
<211> LENGTH: 20
<212> TYPE: DNA
<213> ORGANISM: Homo sapiens

<400> SEQUENCE: 47
acatttgccg cttggataac                                           20
```

```
<210> SEQ ID NO 48
<211> LENGTH: 20
<212> TYPE: DNA
<213> ORGANISM: Homo sapiens

<400> SEQUENCE: 48
gccaagctgt ctcagtgaca                                              20

<210> SEQ ID NO 49
<211> LENGTH: 20
<212> TYPE: DNA
<213> ORGANISM: Homo sapiens

<400> SEQUENCE: 49
cagtctgacc agcgtgaaaa                                              20

<210> SEQ ID NO 50
<211> LENGTH: 20
<212> TYPE: DNA
<213> ORGANISM: Homo sapiens

<400> SEQUENCE: 50
ggccatccaa atctgtccta                                              20

<210> SEQ ID NO 51
<211> LENGTH: 20
<212> TYPE: DNA
<213> ORGANISM: Homo sapiens

<400> SEQUENCE: 51
ctgcggtcat ctctcaatga                                              20

<210> SEQ ID NO 52
<211> LENGTH: 20
<212> TYPE: DNA
<213> ORGANISM: Homo sapiens

<400> SEQUENCE: 52
agcttggtgg tggatgaaac                                              20

<210> SEQ ID NO 53
<211> LENGTH: 20
<212> TYPE: DNA
<213> ORGANISM: Homo sapiens

<400> SEQUENCE: 53
tccaacaggc ctgagaaatc                                              20

<210> SEQ ID NO 54
<211> LENGTH: 20
<212> TYPE: DNA
<213> ORGANISM: Homo sapiens

<400> SEQUENCE: 54
cttgtgaagc aaaagccaca                                              20

<210> SEQ ID NO 55
<211> LENGTH: 20
<212> TYPE: DNA
<213> ORGANISM: Homo sapiens

<400> SEQUENCE: 55
ccacgacaac gaagaaacct                                              20
```

```
<210> SEQ ID NO 56
<211> LENGTH: 20
<212> TYPE: DNA
<213> ORGANISM: Homo sapiens

<400> SEQUENCE: 56
cagaagacgc cttaccttcg                                               20

<210> SEQ ID NO 57
<211> LENGTH: 20
<212> TYPE: DNA
<213> ORGANISM: Homo sapiens

<400> SEQUENCE: 57
tacctgtacg aaatcgcacg                                               20

<210> SEQ ID NO 58
<211> LENGTH: 20
<212> TYPE: DNA
<213> ORGANISM: Homo sapiens

<400> SEQUENCE: 58
ctacgccaac atgaactcca                                               20

<210> SEQ ID NO 59
<211> LENGTH: 20
<212> TYPE: DNA
<213> ORGANISM: Homo sapiens

<400> SEQUENCE: 59
gaggtccatg atccactggt                                               20

<210> SEQ ID NO 60
<211> LENGTH: 20
<212> TYPE: DNA
<213> ORGANISM: Homo sapiens

<400> SEQUENCE: 60
gccctactcg tacatctcgc                                               20

<210> SEQ ID NO 61
<211> LENGTH: 20
<212> TYPE: DNA
<213> ORGANISM: Homo sapiens

<400> SEQUENCE: 61
tctcatgttg aagccactgc                                               20

<210> SEQ ID NO 62
<211> LENGTH: 20
<212> TYPE: DNA
<213> ORGANISM: Homo sapiens

<400> SEQUENCE: 62
ggtttgtttt ctcgggttga                                               20

<210> SEQ ID NO 63
<211> LENGTH: 20
<212> TYPE: DNA
<213> ORGANISM: Homo sapiens

<400> SEQUENCE: 63
```
gcagggtcta gaaggctgtg                                               20

<210> SEQ ID NO 64
<211> LENGTH: 20
<212> TYPE: DNA
<213> ORGANISM: Homo sapiens

<400> SEQUENCE: 64
tccctcttcc ctcctcaaat                                               20

<210> SEQ ID NO 65
<211> LENGTH: 20
<212> TYPE: DNA
<213> ORGANISM: Homo sapiens

<400> SEQUENCE: 65
tcagcgtgta aaggcatctg                                               20

<210> SEQ ID NO 66
<211> LENGTH: 20
<212> TYPE: DNA
<213> ORGANISM: Homo sapiens

<400> SEQUENCE: 66
cgacaatctg gttagggaa                                                20

<210> SEQ ID NO 67
<211> LENGTH: 20
<212> TYPE: DNA
<213> ORGANISM: Homo sapiens

<400> SEQUENCE: 67
tggcatctgc tttttgtctg                                               20

<210> SEQ ID NO 68
<211> LENGTH: 20
<212> TYPE: DNA
<213> ORGANISM: Homo sapiens

<400> SEQUENCE: 68
cgcttcataa aagcctcctg                                               20

<210> SEQ ID NO 69
<211> LENGTH: 20
<212> TYPE: DNA
<213> ORGANISM: Homo sapiens

<400> SEQUENCE: 69
caacctttgc cctctaccaa                                               20

<210> SEQ ID NO 70
<211> LENGTH: 20
<212> TYPE: DNA
<213> ORGANISM: Homo sapiens

<400> SEQUENCE: 70
gcttcggtca tgggtctcta                                               20

<210> SEQ ID NO 71
<211> LENGTH: 20
<212> TYPE: DNA
<213> ORGANISM: Homo sapiens

<400> SEQUENCE: 71

-continued

```
<210> SEQ ID NO 72
<211> LENGTH: 20
<212> TYPE: DNA
<213> ORGANISM: Homo sapiens

<400> SEQUENCE: 72
gtggagagct ttgcaggttc                                               20

<210> SEQ ID NO 73
<211> LENGTH: 20
<212> TYPE: DNA
<213> ORGANISM: Homo sapiens

<400> SEQUENCE: 73
cagtttggag ctcctggaag                                               20

<210> SEQ ID NO 74
<211> LENGTH: 20
<212> TYPE: DNA
<213> ORGANISM: Homo sapiens

<400> SEQUENCE: 74
tgcaaatcca gggtgcagtg                                               20
```
ctccacttcc gactctggac                                               20